US012778415B2

(12) United States Patent
Jia et al.

(10) Patent No.: US 12,778,415 B2
(45) Date of Patent: Nov. 3, 2026

(54) SIGNAL ATTENUATION-COMPENSATED AND PROJECTION RESOLVED OPTICAL COHERENCE TOMOGRAPHY ANGIOGRAPHY (SACPR-OCTA)

(71) Applicant: OREGON HEALTH & SCIENCE UNIVERSITY, Portland, OR (US)

(72) Inventors: Yali Jia, Portland, OR (US); Jie Wang, Portland, OR (US)

(73) Assignee: OREGON HEALTH & SCIENCE UNIVERSITY, Portland, OR (US)

( * ) Notice: Subject to any disclaimer, the term of this patent is extended or adjusted under 35 U.S.C. 154(b) by 401 days.

(21) Appl. No.: 18/455,154

(22) Filed: Aug. 24, 2023

(65) Prior Publication Data

US 2024/0065544 A1 Feb. 29, 2024

Related U.S. Application Data

(60) Provisional application No. 63/400,496, filed on Aug. 24, 2022.

(51) Int. Cl.

*A61B 3/10* (2006.01)
*A61B 5/00* (2006.01)
*G06T 5/70* (2024.01)
*G06T 5/92* (2024.01)
*G06T 7/00* (2017.01)

(52) U.S. Cl.

CPC ............ *A61B 3/102* (2013.01); *A61B 5/0066* (2013.01); *A61B 5/7203* (2013.01); *G06T 5/70* (2024.01); *G06T 5/92* (2024.01); *G06T 7/0012* (2013.01); *G06T 2207/10101* (2013.01); *G06T 2207/20021* (2013.01); *G06T 2207/20064* (2013.01);

(Continued)

(58) Field of Classification Search

CPC ............................................ G06T 2207/10101
See application file for complete search history.

(56) References Cited

U.S. PATENT DOCUMENTS 10,231,619 B2 * 3/2019 Huang ................. A61B 3/0025
10,896,490 B2 * 1/2021 Jia ........................... A61B 3/102
2016/0284085 A1 * 9/2016 Huang .................... G06T 7/136
2017/0169590 A1 * 6/2017 Huang ................. A61B 3/0025
2017/0238877 A1 * 8/2017 Hsiao ................... A61B 5/7203
2017/0319060 A1 * 11/2017 Huang ................... A61B 3/102
2018/0182082 A1 * 6/2018 Jia .......................... A61B 3/102

(Continued)

FOREIGN PATENT DOCUMENTS

CN 114387174 A * 4/2022 ............. G06N 3/045
JP 2018187343 A * 11/2018 ........... A61B 5/0066

OTHER PUBLICATIONS

Zhang A, Zhang Q, Wang RK. Minimizing projection artifacts for accurate presentation of choroidal neovascularization in OCT micro-angiography. Biomed Opt Express. Sep. 28, 2015;6(10):4130-43. (Year: 2015).*

(Continued)

*Primary Examiner* — Gandhi Thirugnanam

(74) *Attorney, Agent, or Firm* — Schwabe, Williamson & Wyatt, P.C.

(57) ABSTRACT

Disclosed are methods and systems for signal attenuation-compensated projection-resolved (sacPR) optical coherence tomography angiography (OCTA). The sacPR OCTA may be free of segmentation and vascular contrast enhancement. In some embodiments, projection artifacts may be suppressed with signal compensation including flow and large vessel shadow compensation for projection removal and wavelet-based compensation for noise suppression.

22 Claims, 12 Drawing Sheets
(10 of 12 Drawing Sheet(s) Filed in Color)

(52) U.S. Cl.
CPC ............... *G06T 2207/20201* (2013.01); *G06T 2207/30041* (2013.01)

(56) References Cited

U.S. PATENT DOCUMENTS

| | | | | |
|---|---|---|---|---|
| 2018/0317851 | A1* | 11/2018 | Jia | A61B 3/102 |
| 2018/0344147 | A1* | 12/2018 | Huang | A61B 3/1241 |
| 2019/0069775 | A1* | 3/2019 | Kubach | A61B 3/0058 |
| 2019/0167100 | A1* | 6/2019 | Huang | A61B 3/0025 |
| 2020/0273218 | A1* | 8/2020 | Camino | A61B 3/102 |
| 2021/0045672 | A1* | 2/2021 | Jia | A61B 3/1233 |
| 2021/0153738 | A1* | 5/2021 | Jia | A61B 3/1233 |
| 2021/0358096 | A1* | 11/2021 | Mei | G06T 5/60 |
| 2022/0151490 | A1* | 5/2022 | Jia | A61B 3/102 |
| 2023/0091487 | A1* | 3/2023 | Lee | G06T 5/77<br>382/128 |
| 2023/0196525 | A1* | 6/2023 | Bagherinia | A61B 3/0025<br>382/131 |
| 2023/0320583 | A1* | 10/2023 | Yaikhom | A61B 3/0025<br>351/205 |
| 2024/0065544 | A1* | 2/2024 | Jia | A61B 3/102 |
| 2024/0407643 | A1* | 12/2024 | Wei | A61B 3/102 |

OTHER PUBLICATIONS

Zhang M, Hwang TS, Campbell JP, Bailey ST, Wilson DJ, Huang D, Jia Y. Projection-resolved optical coherence tomographic angiography. Biomed Opt Express. Feb. 9, 2016;7(3):816-28. (Year: 2016).*

Jie Wang, Tristan T. Hormel, Steven T. Bailey, Thomas S. Hwang, David Huang, and Yali Jia, "Signal attenuation-compensated projection-resolved OCT angiography," Biomed. Opt. Express 14, 2040-2054 (2023) (Year: 2023).*

Wang Y, Wei S, Kang JU. Depth-resolved backscattering signal reconstruction based OCT attenuation compensation. Proc SPIE Int Soc Opt Eng. Jan.-Feb. 2022; (Year: 2022).*

Yali Jia, Ou Tan, Jason Tokayer, Benjamin Potsaid, Yimin Wang, Jonathan J. Liu, Martin F. Kraus, Hrebesh Subhash, James G. Fujimoto, Joachim Hornegger, and David Huang, "Split-spectrum amplitude-decorrelation angiography with optical coherence tomography," Opt. Express 20, 4710-4725 (2012) (Year: 2012).*

Hormel TT, Huang D, Jia Y. Artifacts and artifact removal in optical coherence tomographic angiography. Quant Imaging Med Surg. Mar. 2021;11(3):1120-1133. doi: 10.21037/qims-20-730. PMID: 33654681; PMCID: PMC7829161. (Year: 2021).*

Chaoliang Chen, Weisong Shi, Victor X.D. Yang, Wanrong Gao, Time interval optimized optical coherence tomographic angiography for bulk motion suppression on human skin, Optics Communications, vol. 513,2022, 128077, ISSN 0030-4018,https://doi.org/10.1016/j.optcom.2022.128077. (Year: 2022).*

Wellner, P. D., "Adaptive thresholding for the DigitalDesk," Xerox, EPC1993-110, pp. 1-19 (1993).

Bradley, D., et al, "Adaptive Thresholding Using Integral Image," Journal of Graphics Tools vol. 12, Issue 2, pp. 13-21 (2007).

Wang, J. et al., "Reflectance-based projection-resolved optical coherence tomography angiography," Biomedical Optics Express vol. 8, No. 3, pp. 1536-1548 (2017).

* cited by examiner

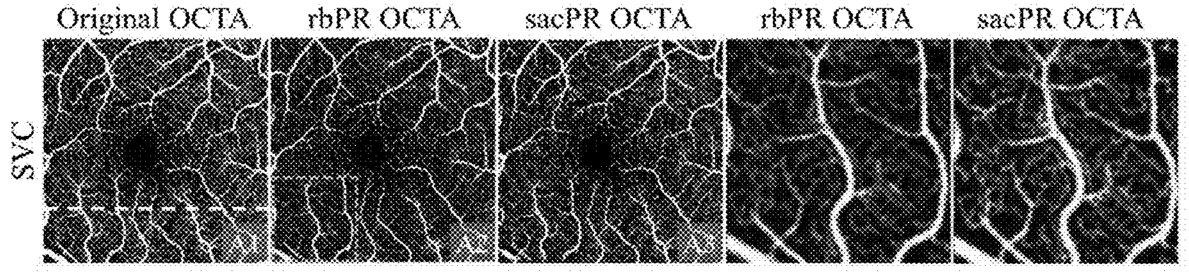
Figure 6A1 Figure 6A2 Figure 6A3 Figure 6A4 Figure 6A5
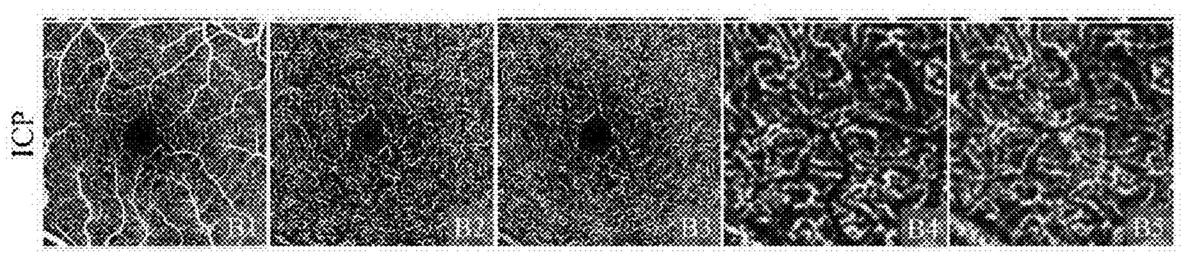
Figure 6B1 Figure 6B2 Figure 6B3 Figure 6B4 Figure 6B5
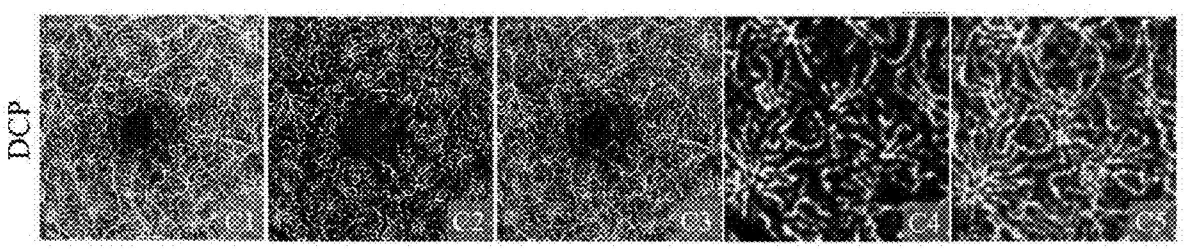
Figure 6C1 Figure 6C2 Figure 6C3 Figure 6C4 Figure 6C5
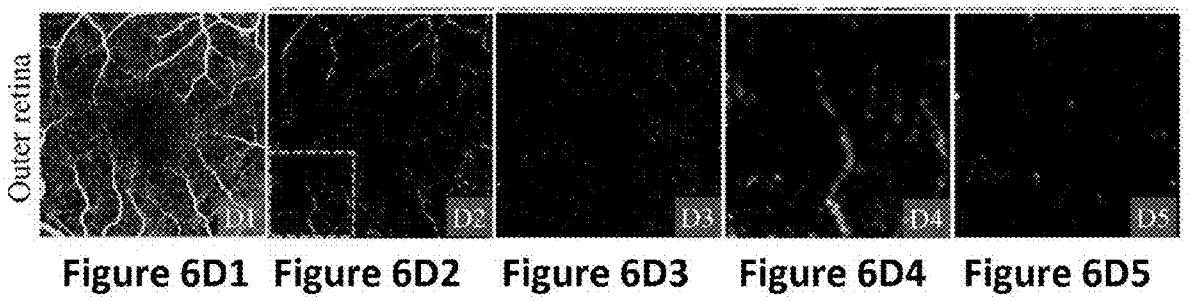
Figure 6D1 Figure 6D2 Figure 6D3 Figure 6D4 Figure 6D5

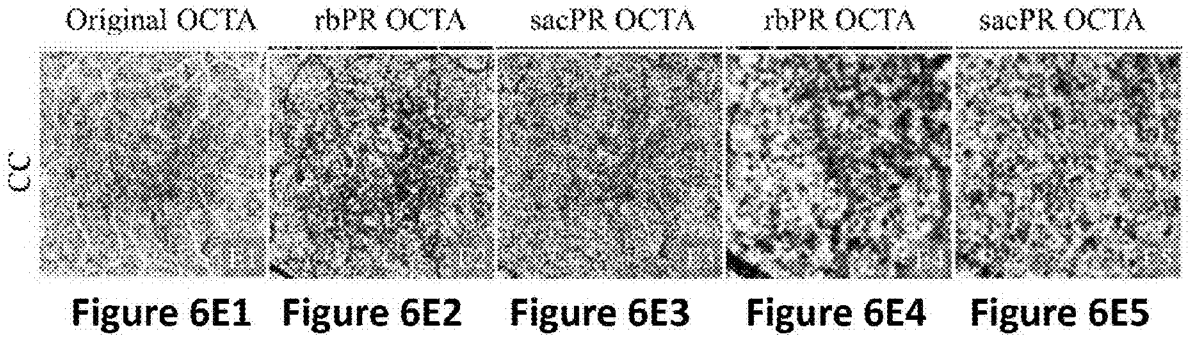
Figure 6E1 Figure 6E2 Figure 6E3 Figure 6E4 Figure 6E5
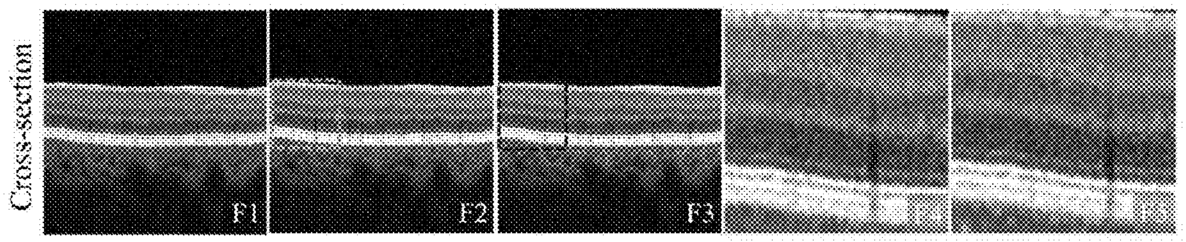
Figure 6F1 Figure 6F2 Figure 6F3 Figure 6F4 Figure 6F5

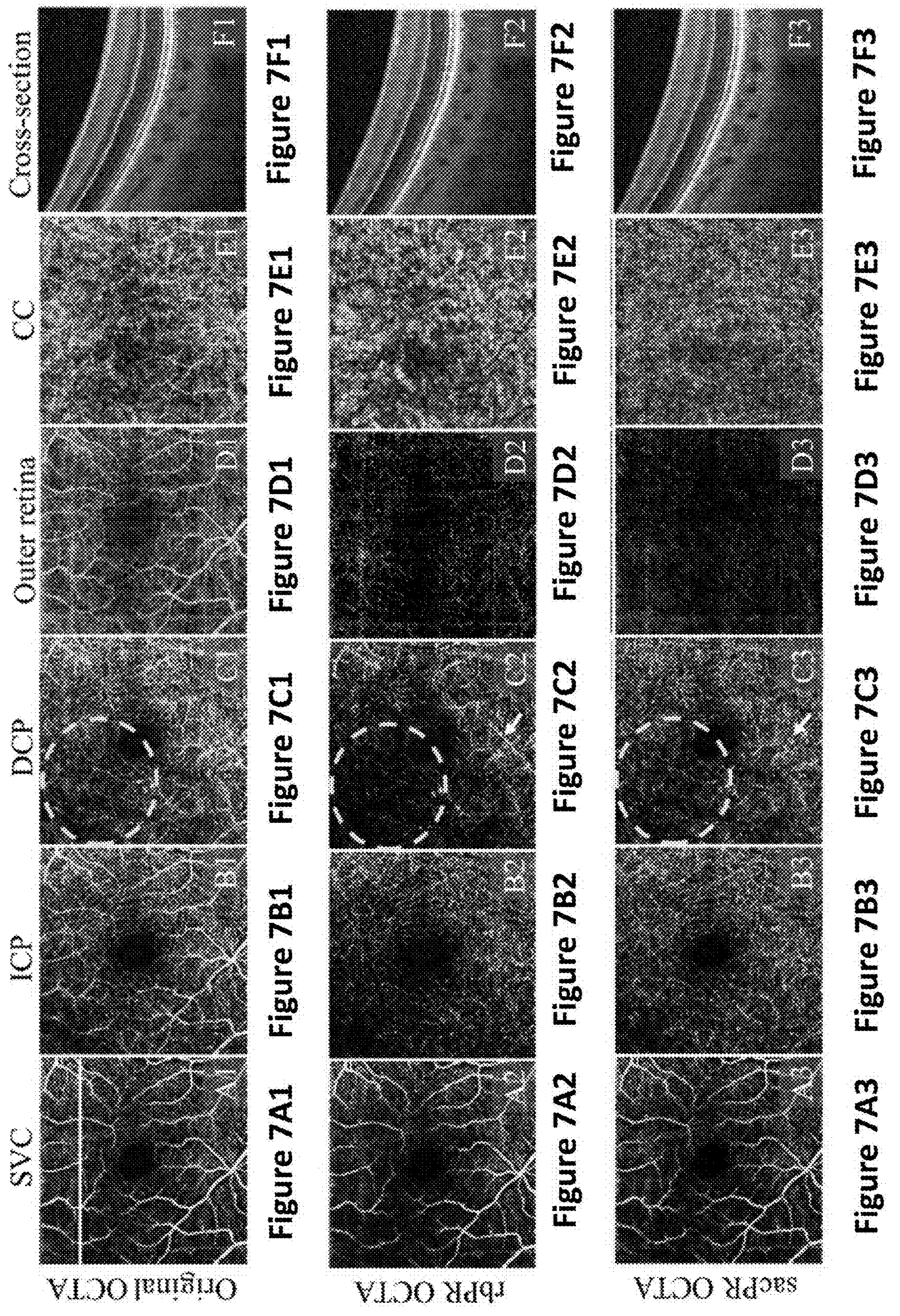
Figure 7A1 Figure 7B1 Figure 7C1 Figure 7D1 Figure 7E1 Figure 7F1
Figure 7A2 Figure 7B2 Figure 7C2 Figure 7D2 Figure 7E2 Figure 7F2
Figure 7A3 Figure 7B3 Figure 7C3 Figure 7D3 Figure 7E3 Figure 7F3

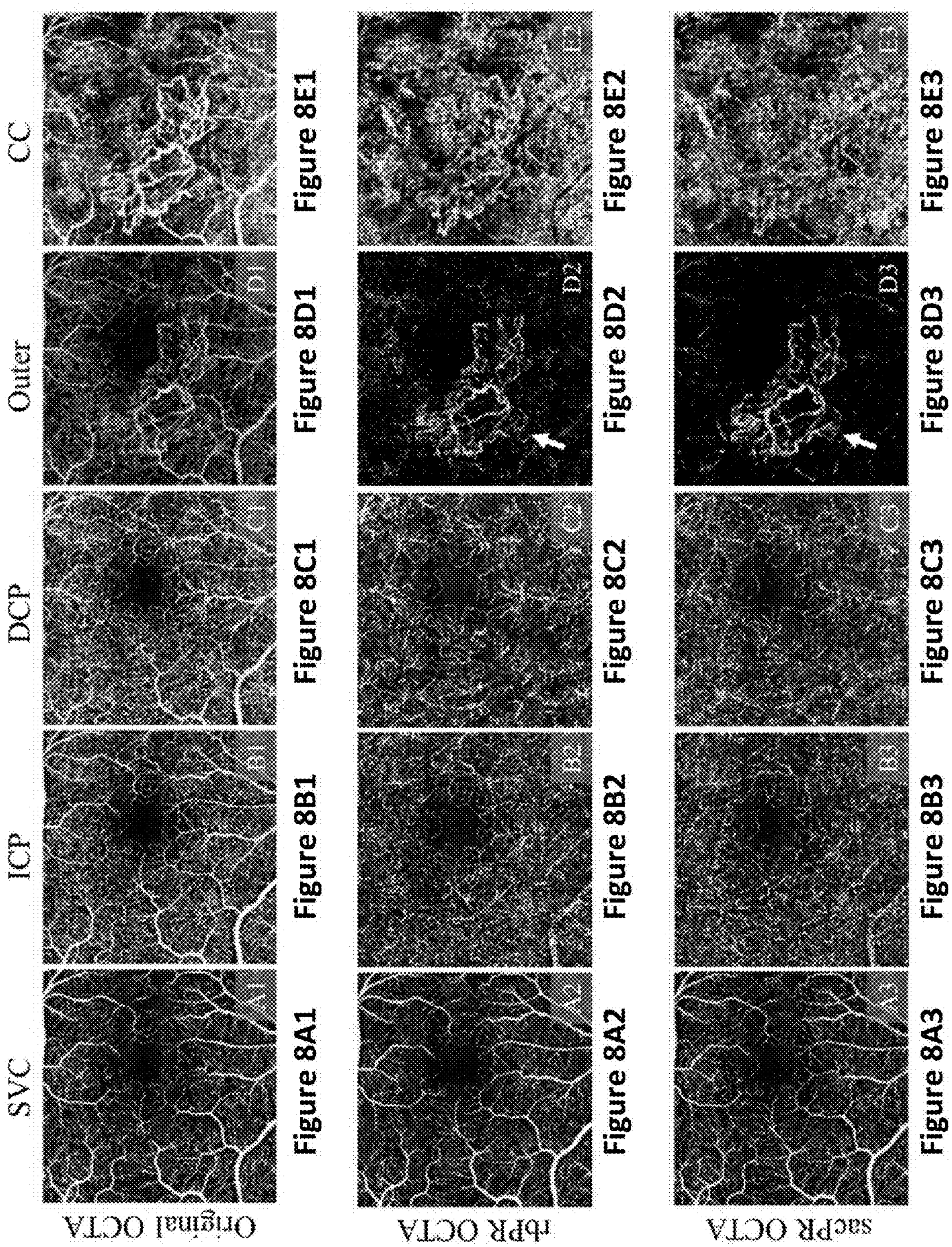
SVC
ICP
DCP
Outer
CC
Original OCTA
rbPR OCTA
sacPR OCTA
Figure 8A1
Figure 8B1
Figure 8C1
Figure 8D1
Figure 8E1
Figure 8A2
Figure 8B2
Figure 8C2
Figure 8D2
Figure 8E2
Figure 8A3
Figure 8B3
Figure 8C3
Figure 8D3
Figure 8E3

Figure 9A1 Figure 9B1 Figure 9C1 Figure 9D1
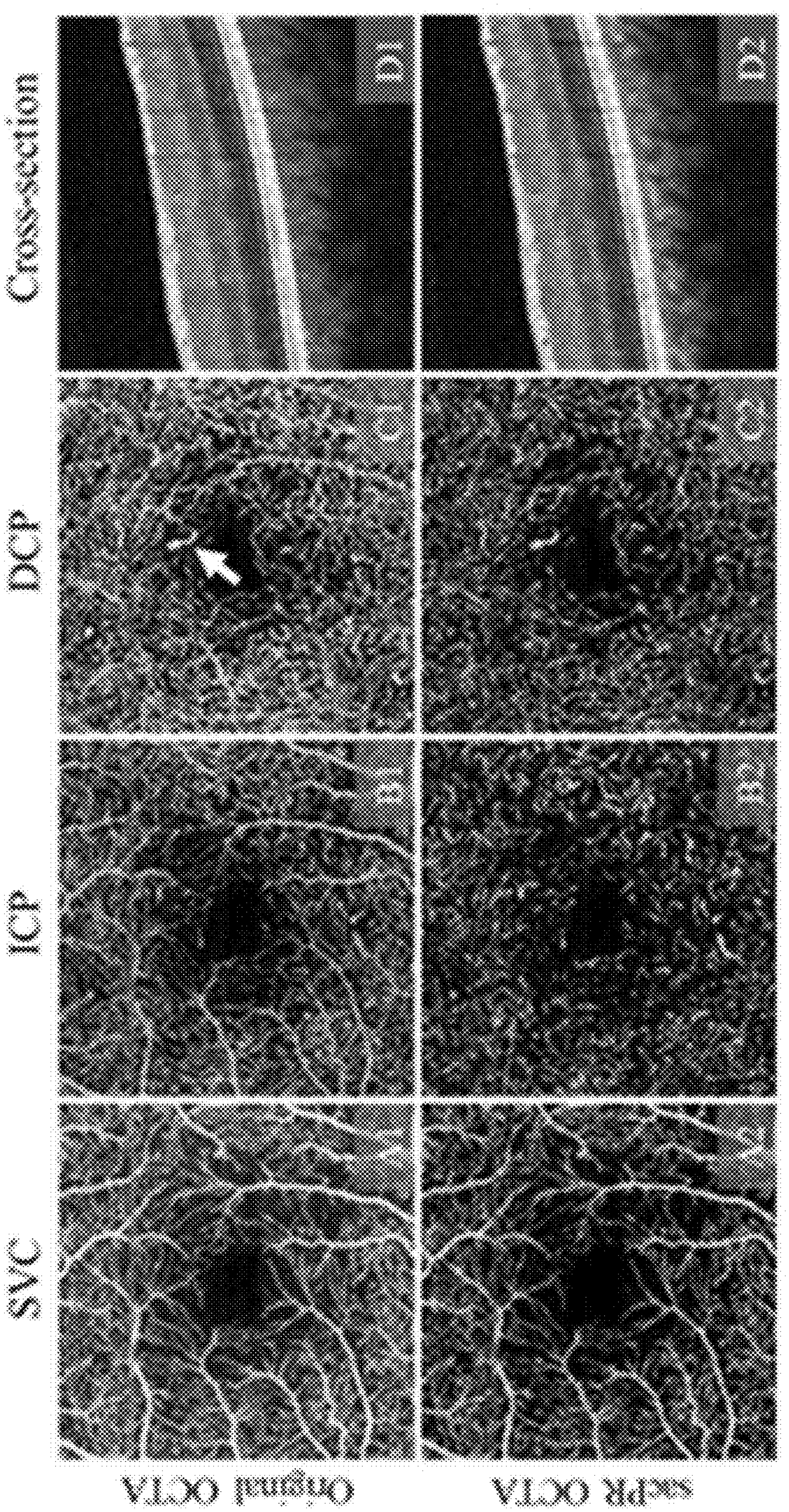
Figure 9A2 Figure 9B2 Figure 9C2 Figure 9D2

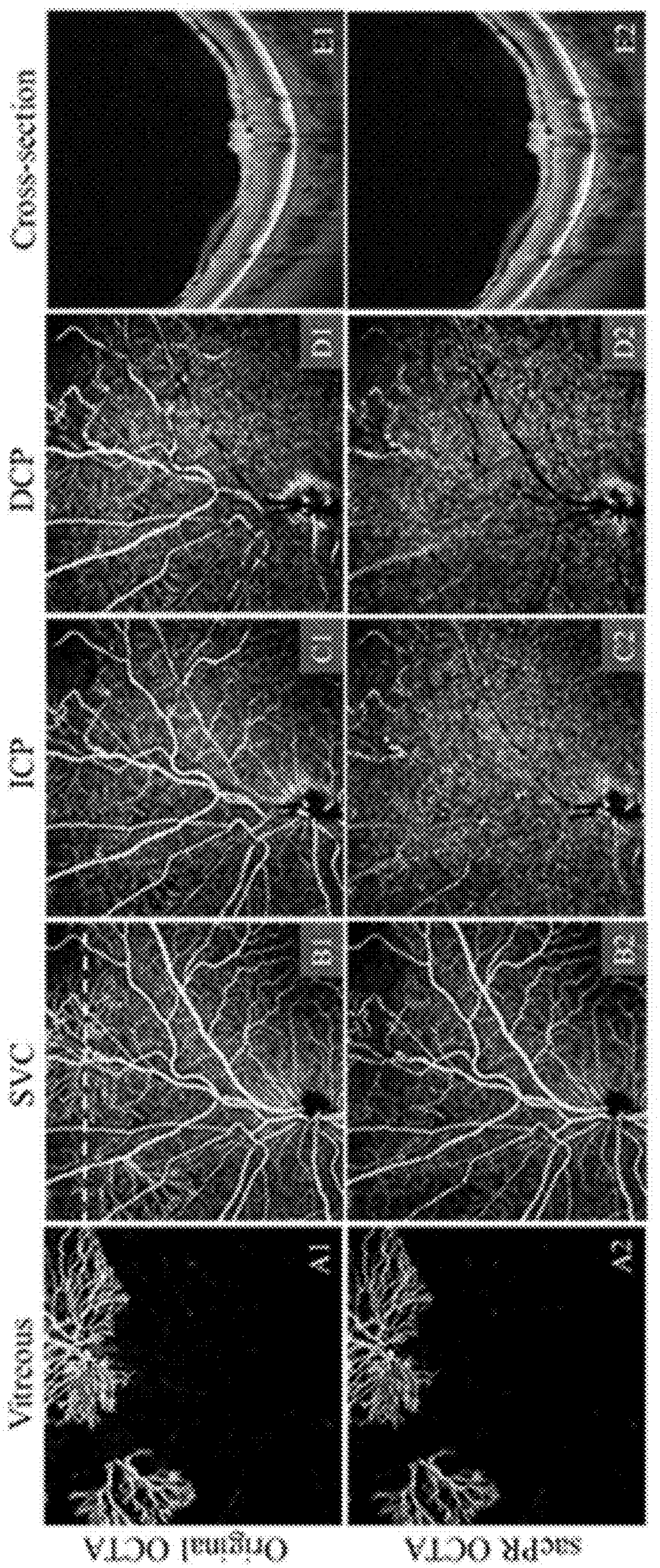
Figure 10A1 Figure 10B1 Figure 10C1 Figure 10D1 Figure 10E1
Figure 10A2 Figure 10B2 Figure 10C2 Figure 10D2 Figure 10E2

SIGNAL ATTENUATION-COMPENSATED AND PROJECTION RESOLVED OPTICAL COHERENCE TOMOGRAPHY ANGIOGRAPHY (SACPR-OCTA)

CROSS REFERENCE TO RELATED APPLICATION

The present application claims priority to U.S. Provisional Patent Application No. 63/400,496, filed Aug. 24, 2022, entitled "SIGNAL ATTENUATION-COMPENSATED AND PROJECTION RESOLVED OPTICAL COHERENCE TOMOGRAPHY ANGIOGRAPHY (SACPR-OCTA)," the entire disclosure of which is hereby incorporated by reference.

ACKNOWLEDGEMENT OF GOVERNMENT SUPPORT

This invention was made with the support of the United States government under the terms of grant numbers R01 EY024544 and R01 EY027833 awarded by the National Institutes of Health. The government has certain rights to this invention.

FIELD

Generally, the field involves imaging using optical coherence tomography. In particular, the field involves methods, apparatuses, and systems for signal attenuation-compensated and projection-resolved optical coherence tomography angiography (sacPR-OCTA).

BACKGROUND

Since the first time-domain optical coherence tomography (OCT) article was published in 1991, OCT technology has been developed rapidly and successfully applied in the ophthalmology field by providing high-definition and depth-resolved retinal structural volume. With faster scanning using Fourier-domain and swept-source imaging modalities, current OCT devices allow acquisition of three-dimensional data representing the retinal layered structure rapidly. Optical coherence tomographic angiography (OCTA) is one of the most successful OCT extensions that detects the variation of OCT signal reflectance over scans repeated at the same location to evaluate the microcirculation flow in vivo. OCTA allows sensitive, non-invasive, non-dye-based, fast-speed, high-resolution and depth-resolved volumetric imaging of the retinal and choroidal circulatory networks in vivo at capillary-scale detail. Previous studies have demonstrated that OCTA has many of the features needed to replace traditional imaging modalities, such as fluorescein angiography (FA) and indocyanine green angiography (ICGA) in precise diagnosis and measurements of eye diseases.

However, a major limitation of OCTA as originally proposed is artifacts, including projection, shadow and motion artifacts. Each of these is due to the way that OCTA data is acquired and processed, and manifest differently in the images. Projection artifacts are particularly challenging because they cause specious flow signals mimicking the morphology of superficial vasculature to appear in deeper anatomic layers.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

FIGS. 1A, 1A1, 1A2, 1A3, and 1B-1F illustrate uncorrected OCTA exhibiting projection artifacts. FIG. 1A illustrates a cross-sectional structural OCT overlaid with color coded OCTA flow in the inner retina (violet), outer retina (yellow) and choroid (red). FIG. 1A1 is the magnified region highlighted with the dashed box in FIG. 1A. The structural and flow signal in FIG. 1A1 are separated for illustrative purposes in FIGS. 1A2 and 1A3. Other OCT angiograms shown are maximum projections of the SVC (FIG. 1B), ICP (FIG. 1C), DCP (FIG. 1D), outer retina (FIG. 1E), and choriocapillaris (FIG. 1F). The SVC refers to the superficial vascular complex defined as the anterior 80% of the ganglion cell complex (GCC); ICP refers to the intermediate capillary plexus defined as the outer 20% of the ganglion cell complex and inner 50% of the inner nuclear layer (INL); DCP refers to the deep capillary plexus defined as the outer 50% of the INL and the outer plexiform layer (OPL); the outer retina is defined as the lower boundary of OPL to Bruch's membrane (BM); the CC corresponds to the choriocapillaris and is defined as the region between BM and BM+10 um.

FIGS. 2A-2E, 2F1, 2F2, 2G, 2H1, and 2H2 illustrate large vessel shadow compensation in structural OCT. FIG. 2A is a 3D structural OCT; FIG. 2B is a cross-section structural image at the position of white arrow pointed in FIG. 2A, overlaid with a tissue mask (red) made using a 3D adaptive thresholding algorithm; FIG. 2C is a cross-section structural OCT overlaid with the color-coded cumulative map calculated on each A-line; FIG. 2D is a cross-sectional structural OCT overlaid with a superficial region mask (green) with cumulative sum higher than 0.9 mm; FIG. 2E is an OCT angiogram generated in the superficial region using maximum projection; FIG. 2F1 illustrates the enhanced vasculature; FIG. 2F2 is the enhanced en face OCT angiogram obtained by multiplying the enhanced vasculature and original OCT angiogram for suppressing the background noise; FIG. 2G illustrates large vessel mask detected by OTSU's thresholding algorithm; FIG. 2H1 is the original cross-sectional OCT with large vessel shadow; and FIG. 2H2 is the large vessel shadow compensated cross-sectional OCT.

FIG. 3A is a cross-sectional structural OCT overlaid with the sacPR-OCTA color coded according to anatomic location (violet: inner retina, yellow: outer retina, red: choroid). FIG. 3B illustrates a superficial vascular complex (SVC). FIG. 3C illustrates an intermediate capillary plexus (ICP). FIG. 3D illustrates a deep capillary plexus (DCP).

FIG. 5A illustrates cross-sectional structural OCT overlaid with color coded sacPR-OCTA, demonstrating that projection artifact tails have been successfully suppressed (violet: inner retina, yellow: outer retina, red: choroid). FIG. 5B illustrates the SVC. FIG. 5C illustrates ICP. FIG. 5D illustrates the DCP.

FIGS. 6A1-6A5, 6B1-6B5, 6C1-6C5, 6D1-6D5, 6E1-6E5, and 6F1-6F5 illustrate a comparison of original OCTA from a normal subject with projection artifacts (column 1, FIGS. 6A1-6F1), with projection artifacts removal using reflectance-based projection-resolved OCTA algorithm (rbPR-OCTA, column 2, FIGS. 6A2-6F2) and the sacPR-OCTA (column 3, FIGS. 6A3-6F3). Column 4 (FIGS. 6A4-6F4) illustrates magnified angiograms in regions of respective FIGS. 6A2-6F2 highlighted by green boxes in FIG. 6A2. Column 5 (FIGS. 6A5-6F5) illustrates magnified angiograms in regions of respective FIGS. 6A3-6F3 highlighted by blue boxes in FIG. 6A3. Rows 1-5 correspond to en face OCT angiograms of SVC, ICP, DCP, outer retina, and sub-macular CC, respectively. Row 6 illustrates cross-sectional structural OCT overlaid with color coded flow signal (violet: inner retina, yellow: outer retina, red: choroid) at the position indicated by the white dotted line in FIG. 6A1.

FIGS. 7A1-7A3, 7B1-7B3, 7C1-7C3, 7D1-7D3, 7E1-7E3, and 7F1-7F3 illustrate a comparison of PR OCTA algorithms on a scan with shadow artifacts. Rows 1-3 illustrate original, rbPR, and sacPR OCTA, respectively. Columns A-E correspond to en face angiograms of the SVC, ICP, DCP, outer retina, and sub-macular CC, respectively. Column F are cross-sectional structural OCT images overlaid with color coded flow signals (violet: inner retina, yellow: outer retina, red: choroid).

FIGS. 8A1-8A3, 8B1-8B3, 8C1-8C3, 8D1-8D3, 8E1-8E3 illustrate a comparison of PR OCTA algorithms on the neovascular AMD with CNV. Rows 1-3 correspond to original, rbPR, and sacPR OCTA, respectively. Columns A-E are en face angiograms of SVC, ICP, DCP, outer retina, and sub-macular CC, respectively. The sacPR OCTA algorithms reserved more real CNV signals (highlighted by white arrows).

FIGS. 9A1-D1 and 9A2-D2 illustrate sacPR OCTA on angioplex 3×3-mm scan. Rows 1 and 2 illustrate original and sacPR OCTA, respectively. Columns A-C are en face angiograms of SVC, ICP, and DCP, respectively. Column D illustrates cross-sectional structural OCT overlaid with color coded flow signals (violet: inner retina, yellow: outer retina, red: choroid). The white arrow highlights the dilated vessel in DCP.

FIGS. 10A1-10E1 and 10A2-10E2 illustrate sacPR OCTA on Solix 9×9-mm scan. Rows 1 and 2 illustrate original and sacPR OCTA, respectively. Columns A-C are en face angiograms of SVC, ICP, DCP, respectively. Column D is cross-sectional structural OCT overlaid with color coded flow signals (gold: vitreous, violet: inner retina, yellow: outer retina, red: choroid. The red arrow highlights the connection between the NV and feeder vessel.

DETAILED DESCRIPTION

Figures 1B, 1C, 1D, 1E, 1F:
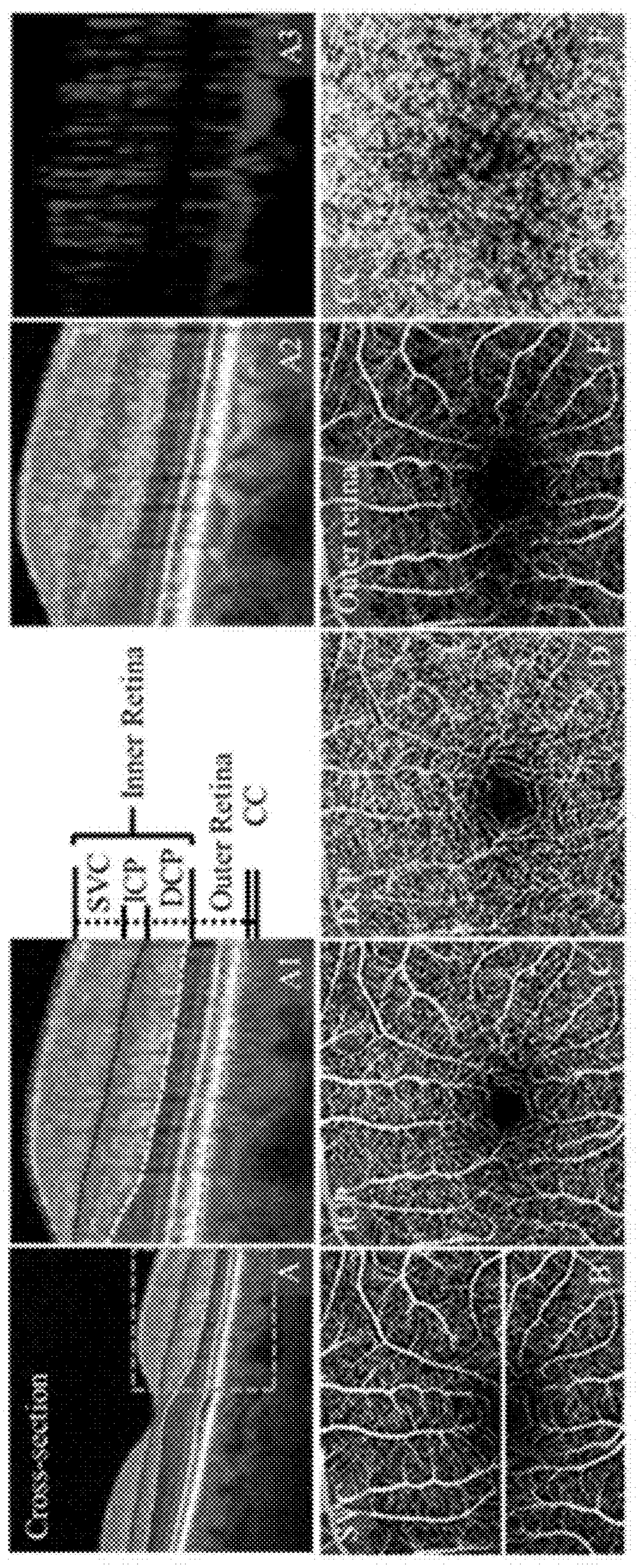

Disclosed are methods and systems for signal attenuation-compensated projection-resolved (sacPR) OCTA. The sacPR OCTA may be free of segmentation and vascular contrast enhancement. In some embodiments, projection artifacts may be suppressed based on signal attenuation, with signal compensation including flow and large vessel shadow compensation for projection removal and wavelet-based compensation for noise suppression. Quantitative results are also provided herein, which demonstrate that the sacPR-OCTA technique improves the vascular integrity and signal-to-noise ratio in normal control subjects compared to a current state-of-the-art approach. Additionally, the sacPR-OCTA technique better preserve flow signal in choroidal neovascular lesions and shadowing area. Furthermore, sacPR-OCTA processes the data in each normalized A-line, and is independent to different platforms with different OCTA algorithms and imaging resolution.

Also disclosed herein is an exemplary system for performing sacPR-OCTA using the disclosed methods. The exemplary system comprises an OCT device configured to acquire OCT structural and/or angiography data in functional connection with a computing device having a logic subsystem and data holding capabilities. In embodiments the computing device is configured to receive data from the OCT device and perform one or more operations of the methods described herein.

In the following detailed description, reference is made to the accompanying drawings which form a part hereof, and in which are shown by way of illustration embodiments that can be practiced. It is to be understood that other embodiments can be utilized and structural or logical changes can be made without departing from the scope. Therefore, the following detailed description is not to be taken in a limiting sense, and the scope of embodiments is defined by the appended claims and their equivalents.

Various operations can be described as multiple discrete operations in turn, in a manner that can be helpful in understanding embodiments; however, the order of description should not be construed to imply that these operations are order dependent.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, structure and/or flow information of a sample can be obtained using OCT (structure) and OCT angiography (flow) imaging-based on the detection of spectral interference. Such imaging can be two-dimensional (2-D) or three-dimensional (3-D), depending on the application. Structural imaging can be of an extended depth range relative to prior art methods, and flow imaging can be performed in real time. One or both of structural imaging and flow imaging as disclosed herein can be enlisted for producing 2-D or 3-D images.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

All publications, patent applications, patents, and other references mentioned herein are incorporated by reference in their entirety. In case of conflict, the present specification, including explanation of terms, will control. In addition, the methods, systems, apparatuses, materials, and examples are illustrative only and not intended to be limiting.

In order to facilitate review of the various embodiments of the disclosure, the following explanation of specific terms is provided:

A-scan: A reflectivity profile that contains information about spatial dimensions and location of structures within an item of interest. An A-scan is an axial scan directed along the optical axis of the OCT device and penetrates the sample being imaged. The A-scan encodes reflectivity information (for example, signal intensity) as a function of depth (z-direction).

B-scan: A cross-sectional tomograph that can be achieved by laterally combining a series of axial depth scans (i.e., A-scans) in the x-direction or y-direction. A B-scan encodes planar cross-sectional information from the sample and is typically presented as an image. Thus, a B-scan can be called a cross sectional image.

Dataset: As used herein, a dataset is an ordered-array representation of stored data values that encodes relative spatial location in row-column-depth (x-y-z axes) format. In the context of OCT, as used herein, a dataset can be conceptualized as a three dimensional array of voxels, each voxel having an associated value (for example, an intensity value, a complex value having both amplitude and phase information, a decorrelation value, or other signal representations). An A-scan corresponds to a set of collinear voxels along the depth (z-axis) direction of the dataset; a B-scan is made up of set of adjacent A-scans combined in the row or column (x- or y-axis) directions. Such a B-scan can also be referred to as an image, and its constituent voxels referred to as pixels. A collection of adjacent B-scans can be combined form a 3D volumetric set of voxel data referred to as a 3D image. In the system and methods described herein, the dataset obtained by an OCT scanning device is termed a "structural OCT" dataset whose values can, for example, be complex numbers carrying intensity and phase information. This structural OCT dataset can be used to calculate a corresponding dataset termed an "OCT angiography" dataset reflecting flow within the imaged sample. There is a correspondence between the voxels of the structural OCT dataset and the OCT angiography dataset. Thus, values from the datasets can be "overlaid" to present composite images of structure and flow (e.g., tissue microstructure and blood flow) or otherwise combined or compared.

En Face angiogram: OCT angiography data can be presented as a 2D projection of the three dimensional dataset onto a single planar image called an en face angiogram. Construction of such an en face angiogram requires the specification of the upper and lower depth extents that enclose the region of interest within the retina OCT scan to be projected onto the angiogram image. These upper and lower depth extents can be specified as the boundaries between different layers of the retina (e.g., the voxels between the inner limiting membrane and outer plexiform layer could be used to generate an en face angiogram of the inner retina). Once generated, the en face angiogram image may be used to quantify various features of the retinal vasculature as described herein. This quantification typically involves the setting of a threshold value to differentiate, for example, the pixels that represent flow within vasculature from static tissue within the angiogram. These en face angiograms can be interpreted in a manner similar to traditional angiography techniques such as fluorescein angiography (FA) or indocyanine green (ICG) angiography, and are thus well-suited for clinical use. It is also common to generate en face images from structural OCT data in a manner analogous to that used to generate en face angiograms. Angiograms from different layers may also be color-coded and overlaid to present composite angiograms with encoded depth information; structural en face images may also be included in such composite image generation.

Functional OCT, as used herein, broadly refers to the extension of OCT techniques to provide information beyond structural characterization. For example, whereas structural OCT imaging may be used to gather spatial information about a tissue's anatomical organization, functional OCT may be used to gather information about processes occurring within that tissue sample such as blood flow, tissue perfusion and oxygenation, birefringence, etc. Examples of functional OCT include, but are not limited to, OCT angiography (OCTA) and associated techniques for characterizing blood flow, Doppler OCT, polarization-sensitive OCT, OCT elastography, spectroscopic OCT, differential absorption OCT, and molecular imaging OCT.

As discussed above, projection artifacts are one of the major limitations on OCTA. Prior techniques for removal of projection artifacts were reliant on the subtraction of superficial flow signal from deeper slabs; however, the projection artifacts were not able to be removed in cross-sections, and the vascular integrity was inevitably disrupted in deeper slabs which could cause the misdiagnosis of macular ischemia and choroidal neovascularization (CNV). To suppress the projection artifacts by voxel, the present inventors developed a reflectance-based projection resolved (rbPR) OCTA algorithm, which enhanced the real flow signal and suppressed artifacts using vascular contrast on structural volume. Clear vascular networks in deeper slabs and CNV vasculature can help to achieve accurate quantification of nonperfusion area and CNV. In studies, projection resolved OCTA has proven that macular ischemia in three retinal vascular plexuses is associated with diabetic retinopathy severity. Further, projection resolved OCTA can better characterize CNV and perform accurate measurement of CNV which is helpful to track treatment response and CNV growth rate to predict the conversion of nonexudative CNV (for which no treatment is indicated) to exudative CNV (which is currently treated with antiangiogenic therapies). A reliable projection resolved OCTA algorithm is essential for accurate measurements of vascular abnormalities, such as macular ischemia and CNV. However, two major limitations remain in the prior reflectance-based projection resolved OCTA algorithm, as it is reliant on (1) inner/outer retina segmentation since the retinal structural volume was split into two sub-volumes along inner/outer retina boundary, and (2) vascular contrast in structural C-scans. Manual correction of the inner/outer retina boundary is necessary on scans with outer retinal disorders (such as macular edema) where contrast vanishes, and on low-quality scans with defocus or signal attenuation. Accordingly, embodiments herein provide a novel projection resolved OCTA algorithm to get rid of the over-reliance on reflectance contrast and inner/outer segmentation.

In studies conducted by the present inventors, it is found that the detected flow strength is associated with the reflectance strength that is acquired by evaluating the backscattered light. The amplitude of light attenuates while propagating deeper due to scattering and absorption. According to the Beer-Lambert law, the absorptivity is associate with optical path length. Thus, the projection artifacts attenuation also has some connection with the optical path depth. In embodiments herein, the attenuation factors (e.g., reflectance and depth) of OCTA may be used to estimate attenuation of projection artifacts, and the real flows are expected to be higher than the estimated attenuated projection artifacts.

Various embodiments herein may include signal attenuation-compensated projection-resolved (sacPR) OCTA. The sacPR OCTA may be free of segmentation and vascular contrast enhancement. In some embodiments, projection artifacts may be suppressed based on signal attenuation, with signal compensation including flow and large vessel shadow compensation for projection removal and wavelet-based compensation for noise suppression.

OCTA Signal Attenuation Compensation

As an interferometric measurement, OCTA signals can be generated by measuring motion contrast using the amplitude (the magnitude of real and imaginary components), phase (the angle of real and imaginary components), or complex (combining both amplitude and phase) signal from repeated structural B-scans acquired at the same location. While the majority of the collected signal can be attributed to single scattering events in which a photon is backscattered directly to the detector, multiple scattering events, in which a photon scattered more than once before returning to the detector, also occur. Since OCTA resolves depth by identifying the total path length of a photon's trajectory with anatomic depth, multiple scattering events can map the motion contrast signal to the incorrect position. In structural OCT, where the number of multiply scattered photons used to construct the image in a given voxel is always much smaller than the number of single scattered photons, this mistaken signal is not detectable. However, in OCTA multiple scattering events that produce motion contrast, such as a photon being scattered by a blood cell before being backscattered to the detector, can be the primary source of signal. This is the mechanism that produces projection artifacts, which can be identified in cross-section as "tails" (FIG. 1 A) and in en face images as the duplication of superficial vascular patterns in deeper anatomic slabs (FIG. 1 B-F).

The detected flow value S at a voxel can be regarded as a function contributed by the anatomic in-situ flow within the voxel $S_i$, projection artifacts $S_a$ and system noise $S_n$ present:

$$S=f(S_i,S_a,S_n) \tag{1}$$

For static tissue, $S_i=0$, from which is already clear that the signal from multiple scattering events can be the primary contributer to the detected flow signal. The task for projection artifact removal is defining the inverse function $f^{-1}(\cap)$ and restoring the in-situ flow $S_i$ from the observed value S by:

$$S_i=f^{-1}(S) \tag{2}$$

In the implementation, the task of projection artifacts removal can be simplified by estimating the proportion (p) of the in-situ flow contributed in the observed original value, by:

$$S_i=pS \tag{3}$$

The estimation of p for each voxel is the key to extracting the in-situ flow values from the observed flow value that may be affected by projection artifacts. In a previous reflectance-based projection-resolved (rbPR) OCTA study by the present inventors (J. Wang, M. Zhang, T. S. Hwang, S. T. Bailey, D. Huang, D. J. Wilson, and Y. Jia, "Reflectance-based projection-resolved optical coherence tomography angiography," Biomedical optics express 8, 1536-1548 (2017), incorporated by reference herein), the proportion p was estimated based on the vascular contrast in structural OCT. It was observed that vessels in the inner retina had higher reflectivity than the surrounding tissue, which can be used to differentiate real from the spurious flow. However, the outer retina vessels have reflectivity similar to the tissue in which they are embedded. The uncorrected original OCTA signal is theoretically independent of tissue reflectivity. However, pre/post-processing in OCTA algorithms may re-introduce reflectivity dependence. The amplitude of light attenuates while propagating deeper due to scattering and absorption. The scattering rate is reflected in the structural OCT intensity that is measured by evaluating the backscattered light. According to the Beer-Lambert law, attenuation A obeys:

$$A=kcd \tag{4}$$

where k is the molar attenuation coefficient, c is the concentration, and d is the optical path length. k and c are constants that are the properties of attenuation species. Since the structural OCT strength is related to the tissue properties, we can use it as a representative to replace the k and c to simplify the attenuation model in OCT. The projection artifacts ($S_a$) under the in-situ flow ($S_i$) is supposed to attenuate with going deeper. Considering both the scattering and absorption, the attenuation of projection artifacts is related to the reflectance and optical path length according to:

$$\begin{cases} A = g[R_{oct}(z),\ (z-z_0)] \\ S_a(z) = AS_i(z_0) \end{cases} \tag{5}$$

where, $g(\cap)$ is the model of projection, $R_{oct}(z)$ is the tissue reflectance at depth z, $S_i(z_0)$ is the in-situ flow at depth $z_0$, and $S_a(z)$ is the projection artifacts strength at position z, and $z>z_0$.

However, $g(\cap)$ is unknown. To simplify the model, assuming equation $g(\cap)$ is a linear model, and equation 5 can be converted to:

$$S_{ea}(z) = \begin{cases} \left[\alpha R_{oct}(z) + \beta\left(1 - \frac{z-z_0}{D_{max}}\right)\right] S_i(z_0), & \text{if } (z-z_0) \le D_{max} \\ \alpha R_{oct}(z) S_i(z_0), & \text{if } (z-z_0) > D_{max} \end{cases} \tag{6}$$

where, $S_{ea}(z)$ is the estimated projection artifacts strength at depth z, α, and β are reflectance attenuation coefficients of reflectance and optical path length, $D_{max}$ is the restriction of the optical path length. At the sites of real flows, the detected flow values are supposed to be higher than the estimated attenuated projection artifacts with the blood cells boosting the motion contrast. A soft process to enhance real flows was applied by:

$$p(z)=\mathrm{Nor}(S(z)-S_{ea}(z)) \tag{7}$$

where $\mathrm{Nor}(\cap)$ is the normalization operator.

Applying equation (7) to equation (3), the in-situ flow $S_i(z)$ can be restored by:

$$\text{if } (z-z_0) \le D_{max}: \tag{8}$$

$$S_i(z) = \left\{Nor\left\{S(z) - \left[\alpha R_{oct}(z) + \beta\left(1 - \frac{z-z_0}{D_{max}}\right)\right] S_i(z_0)\right\}\right\} S(z);$$

$$\text{if } (z-z_0) > D_{max}:$$

$$S_i(z) = \{Nor\{S(z) - \alpha R_{oct}(z) S_i(z_0)\}\} S(z).$$

In an example implementation, the structural OCT intensity is normalized to [0, 1] to remove the signal strength variation.

Lame Vessel Shadow Compensation

Due to light attenuation, large anterior vessels can produce shadow artifacts in posterior slabs. This complicates projection artifact removal since the shadow artifacts reduce the structural OCT intensity. Thus, the large vessel shadow graphic artifacts may be enhanced to apply the sac-PR OCTA attenuation model to remove the projection artifacts below the large vessel shadows.

Tissue region (FIG. 2B red) may first be detected in structural OCT using an adaptive thresholding method (e.g., as described in P. D. Wellner, "Adaptive thresholding for the DigitalDesk," Xerox, EPC1993-110, 1-19 (1993); and/or D.

Figures 2A, 2B, 2C, 2D, 2E, 2G:
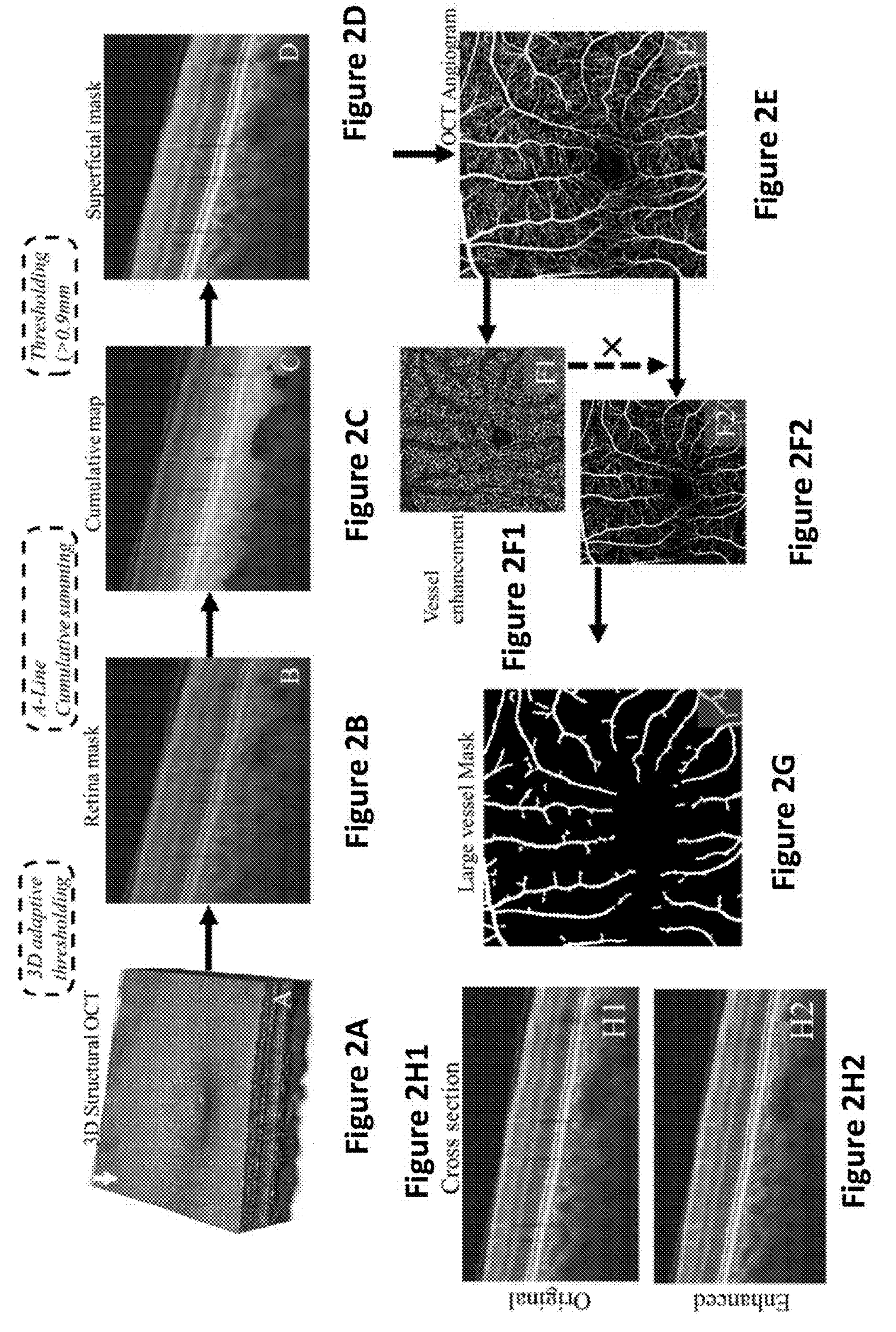
Figure 3A:
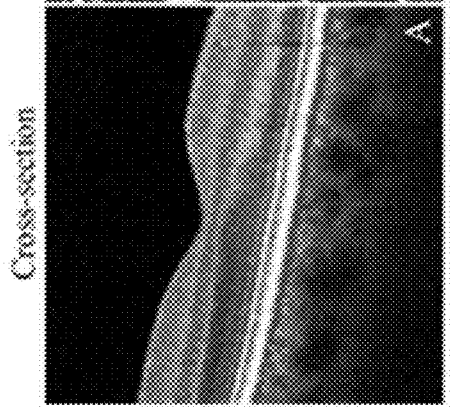
FIGS. 3A-3D illustrate signal attenuation compensated projection resolved (sacPR) OCTA.
Figure 3B:
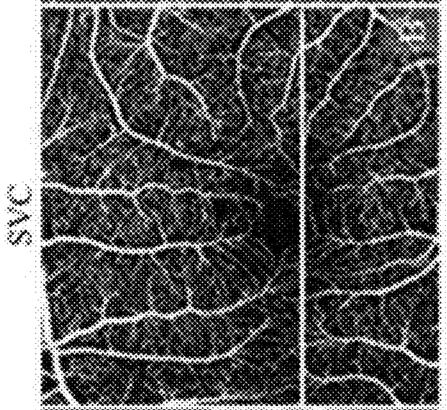
Figure 3C:
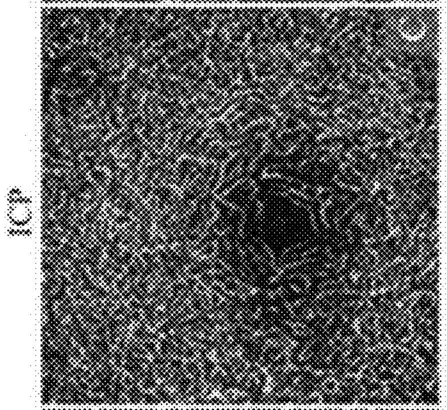
Figure 3D:
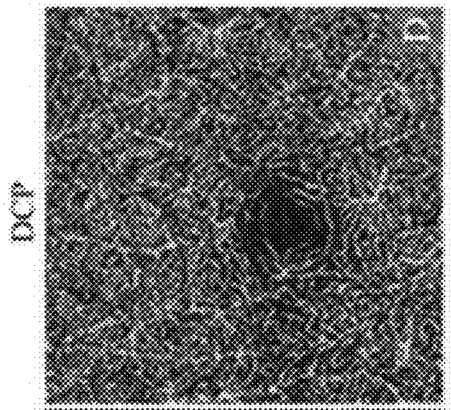

Bradley, and G. Roth, "Adaptive thresholding using the integral image," Journal of graphics tools 12, 13-21 (2007)). Voxels may be classified into two categories, e.g., background with lower intensity and tissues with higher intensity. If the intensity of voxel is higher than the t percentage of the average of surrounding voxels in the $[s_w, s_h, s_d]$ window, and it may be classified as the tissue category. Otherwise, it may be in background category. The values $s_w$, $s_h$, $s_d$ are the window size in height, width and depth, respectively. Then, the cumulative map (FIG. 2C) may be obtained by calculating the cumulative sum on each A-line. The OCT angiogram (FIG. 2E) may be generated in the superficial mask (FIG. 2D) with cumulative sum higher than a certain value, such as 0.9 mm. Retinal vasculature may be further enhanced using vesselness filter and multiplied with original OCT angiogram (FIGS. 2F1 and 2F2). Large vessel mask may be detected from the enhanced the OCT angiogram using a thresholding method and morphological operations (FIG. 2G). The intensity may vary from one side of a large vessel to the other. The intensity of the voxels in large vessel area may be compensated based on the signal strength of the nearest surrounding voxels. The real large vessel's site has higher intensity due to the higher reflectance of blood cells than surrounding tissues. In one example implementation, if the intensity is higher than the average intensity of surrounding tissues, the intensity may be kept as it is; if the intensity is lower than average intensity of surrounding tissues, the intensity of the voxel in large vessel shadow may be multiplied with the ratio between average intensity of surrounding tissues and average intensity of surrounding voxels in large vessel shadow. Compared with the original cross-sectional OCT (FIG. 2H1), large vessel shadows were enhanced in FIG. 2H2, so that the flow signal attenuation compensated model described herein may be applied on the whole volume. The projection artifacts may be removed in voxel, and vessel patterns from upper slab may be removed in intermediate (FIG. 3C) and deep (FIG. 3D) slabs.

OCTA Signal-to-Noise Ratio Compensation Using Wavelet Transform

Figure 4:
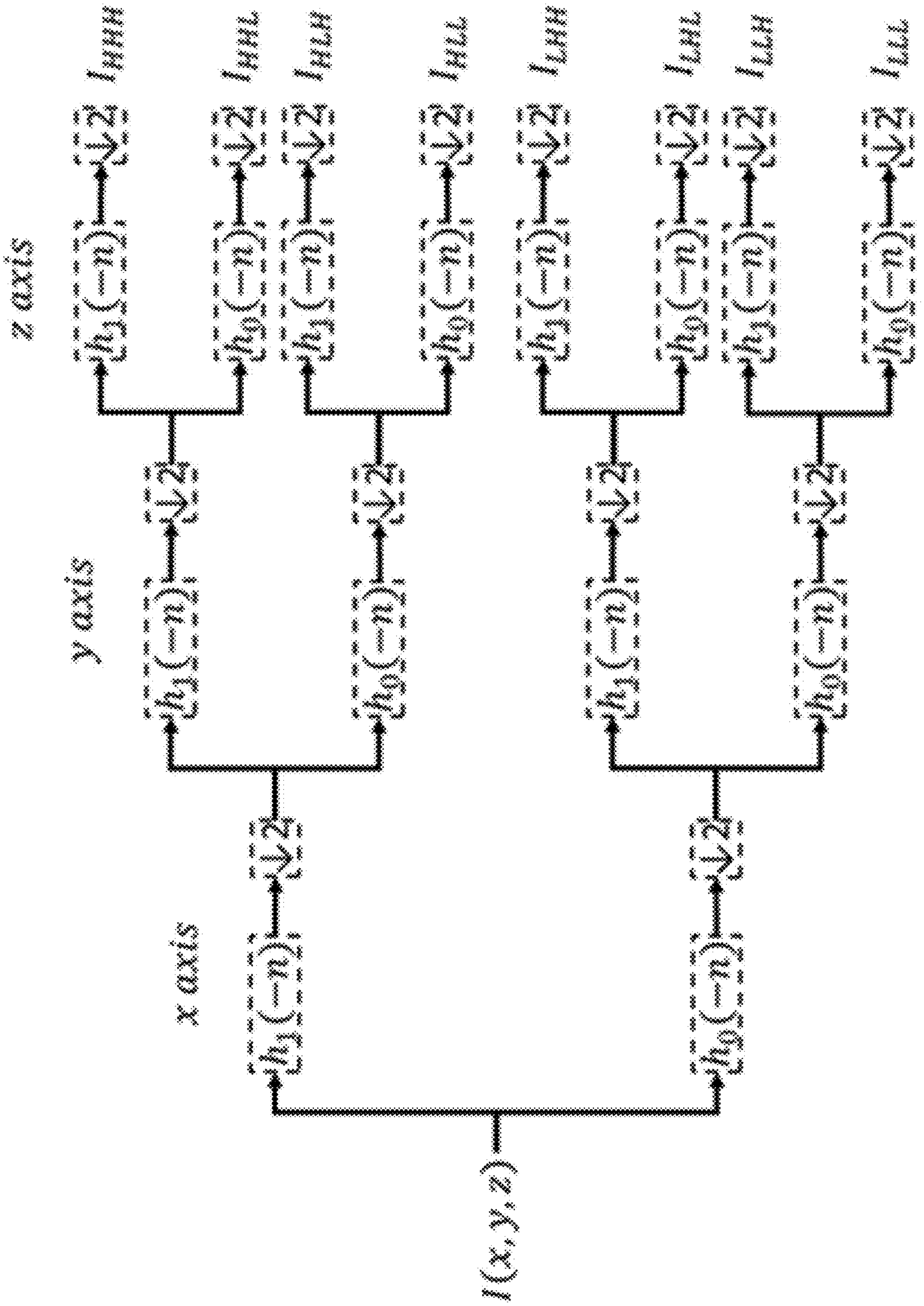
FIG. 4 illustrates wavelet decomposition on volumetric data. h0 and h1 are low and high pass filters, respectively.

Although the enface OCT angiograms of the ICP and DCP generated from sacPR-OCTA show clear capillaries, background noise is also clear. To help suppress remaining noise, wavelet decomposition may be employed in accordance with various embodiments. Similar to Fourier analysis which represents a signal as a summation over sinusoids with varying frequency, wavelet decomposition represents a signal as a summation over wavelets. FIG. 4 shows the wavelet decomposition on the volumetric data.

In practical applications, wavelet decomposition may be conducted sequentially along the horizontal, vertical, and depth directions, respectively. One 3D image may be decomposed into eight components, which are HHH, HHL, HLH, HLL, LHH, LHL, LLH, and LLL with L and H represent low and high frequency, respectively.

Speckle noise and vasculature in OCT angiograms are varying rapidly, both of them have high energy in high frequency components. But the total energy of speckle noise is lower than vessels'; so, coefficients of noise in high frequency components is low. Setting the thresholds on high frequency components is able to remove the noise and reserve the vascular details. The threshold may be implemented according to:

$$I_{(H)} = \begin{cases} \mathrm{sign}(I_{(H)})(|I_{(H)}|), & |I_{(H)}| \geq I_{th} \\ 0, & |I_{(H)}| < I_{th} \end{cases} \quad (9)$$

where $I_{(H)}$ is the high frequency components and $I_{th}$ is the threshold.

The denoised OCTA may be obtained by reconstructing the thresholding processed coefficients.

Figures 5A, 5B, 5C, 5D:
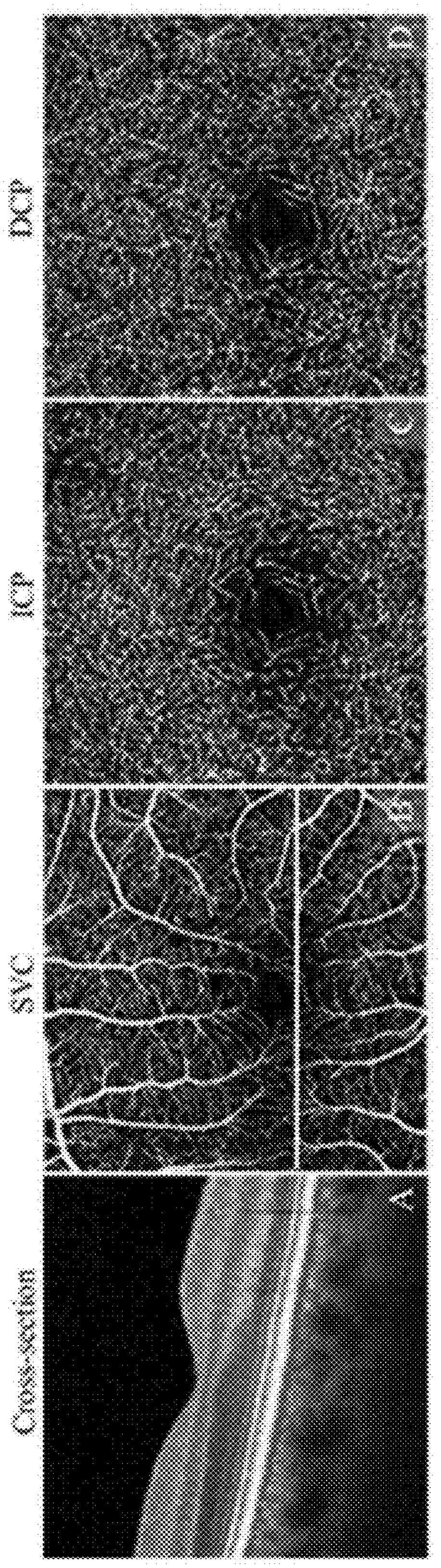
FIGS. 5A-5D illustrate sacPR OCTA with wavelet denoising.

Compared with the initial sacPR-OCTA, background noise (FIGS. 3A-3D) may be significantly suppressed in voxel (FIG. 5A) and showing clear background in fovea avascular zone (FAZ) in en face OCT angiograms (FIGS. 5B-D). The vascular contrast may also be improved.

EXAMPLES

The following examples are illustrative of the disclosed methods. In light of this disclosure, those skilled in the art will recognize that variations of these examples and other examples of the disclosed method would be possible without undue experimentation.

Data Acquisition and Pre-Processing

In one example implementation, participants were scanned using three commercial spectral-domain OCTA systems that were (1) RTVue-XR (Optovue Inc., Fremont, CA) with a center wavelength of 840 nm and 70 kHz axial scan rate, (2) Solix (Optovue Inc., Fremont, CA) with a center wavelength of 840 nm and 130 kHz axial scan rate, and (3) Angioplex (Carl Zeiss, Inc., Dublin, California) with a center wavelength of 840 nm and 68 kHz axial scan rate. In both RTVue-XR and OCTA systems, flow signals were detected using the commercial version of split split-spectrum amplitude-decorrelation angiography (SSADA) algorithm by evaluating the reflectance variation from two consecutive B-scans acquired at same position. One X-fast and one Y-fast volumes were obtained and registered to suppress motion artifacts. The 3×3-mm and 6×6-mm scans were acquired using RTVue-XR system, and 3×3-mm, 6×6-mm, 9×9-mm and 12×12-mm scans were acquired using the Solix system. On the RTVue-XR system, a 3×3-mm volume consists of 304 B-scans and each B-scan consists of 304 A-lines, and a 6×6-mm volume consists of 400 B-scans and each B-scan consists of 400 A-lines. With faster scanning rate, Solix system was able to perform higher scanning density that 3×3-mm volume consists of 400 B-scans and each B-scan consists of 400 A-lines, a 6×6-mm volume consists of 512 B-scans and each B-scan consists of 512 A-lines, a 9×9-mm volume consists of 600 B-scans and each B-scan consists of 600 A-lines.

Retinal neural layers were segmented using the graph search-based algorithm by tracking the boundaries between adjacent nervous tissue slabs on structural OCT volume, including the boundaries of vitreous\inner limiting membrane (ILM), ganglion cell layer (GCL)\inner plexiform layer (IPL), IPL\outer plexiform layer (OPL), OPL\outer nuclear layer (ONL) and Bruch's membrane (BM). Segmentation errors were manually corrected using custom-designed COOL-ART software. Applying retinal layers segmentation of structural OCT to OCTA volume, en face OCT angiograms were generated using maximum projection in multiple slabs including superficial vascular complex (SVC) in the slab of inner 80% of the ganglion cell complex (GCC), intermediate capillary plexus (ICP) in the slab of outer 20% of the GCC and inner 50% of the INL, deep capillary plexus (DCP) in the slab of outer 50% of the INL and OPL, outer retina in the slab between the outer boundary of OPL and BM and choriocapillaris in the slab of BM and BM+10 um.

Experimental Results

The sacPR-OCTA technique described herein was implemented using C++ with OpenCV package and multithreading programming on the computer with Intel® i9-10980XE CPU @ 3.00 GHz. An OCTA scan with standard resolution (640×340×304-pixel) was able to be processed in 0.3~0.5 second.

Evaluation

In uncorrected original OCTA, projection artifacts appear as "tails" descending from vessels in cross-section (FIG. 6F1), while vascular patterns in the SVC are also visibly transposed to the ICP (FIG. 6B1), DCP (FIG. 6C1), outer retina (which is normally avascular; FIG. 6D1), and choriocapillaris (FIG. 6E1). Compared with the previous generation rbPR-OCTA algorithm (FIGS. 6A2-6F2, 6A4-6F4), the described sacPR-OCTA algorithm (FIGS. 6A3-6F3, 6A5-6F5) preserved more flow signal and shows more complete microvascular patterns in deeper slabs including ICP, DCP and CC, especially in the large vessel shadow graphic area, and also suppressed more projection artifacts showing a much cleaner outer retina angiogram. Moreover, the CC is more even using sacPR-OCTA than original OCTA and rbPR, which would benefit analysis exploring biomarkers in diseases associated with the CC.

To evaluate the improvements quantitatively, 109 OCTA scans from 109 eyes were assessed using both rbPR-OCTA and sacPR-OCTA processing by using several metrics, including vessel density (VD), flow signal-to-noise ratio (fSNR), residual artifact strength, and signal correlation between anterior and posterior slabs. To obtain VD in this dataset, OCT angiograms, obtained from the original, rbPR, and sacPR OCTA volume, were binarized using a threshold set at three standard deviations above the average flow value in the fovea avascular zone (FAZ). Foreground pixels are then recognized as vascular, while the background is avascular. VD is then calculated as the percentage of vascular pixels in a region of interest (ROI). Flow signal strength, meanwhile, was evaluated by fSNR from the OCT angiograms by:

$$fSNR = \frac{M_{parafovea} - M_{FAZ}}{\sigma_{FAZ}} \tag{10}$$

where $M_{parafovea}$ is the mean flow value in the parafovea (e.g., defined as the annulus centered on the FAZ with 0.65 mm<|x−$x_c$|<1 mm, where $x_c$ is the FAZ center), and $M_{FAZ}$ and $\sigma_{FAZ}$ are the mean and standard deviation within FAZ.

Remaining projection artifact strength in the outer retina, which is important for the accurate detection and quantification of choroidal neovascularization (CNV) in the normal avascular outer retina, was evaluated by:

$$RA = \frac{M_{outer} + 3 \times \sigma_{outer}}{M_{Inner} + 3 \times \sigma_{Inner}} \tag{11}$$

where $M_{outer}$ and $M_{inner}$ are the mean and $\sigma_{outer}$ and $\sigma_{inner}$ are standard deviations in the outer and inner retina, respectively. Also evaluated was the 3D VD in inner retina volume in which the 3D vascular binary mask was generated by a threshold of the mean plus 3 standard deviations of values of voxels in inner retina volume.

TABLE 1

Comparison between reflectance-based PR and signal attenuation compensation compensated PR on quantitative metrics.

| | | rbPR | sacPR |
|---|---|---|---|
| ICP | VD | 0.38 ± 0.11 | 0.73 ± 0.20 |
| | fSNR | 3.24 ± 1.16 | 9.45 ± 6.10 |
| DCP | VD | 0.32 ± 0.10 | 0.67 ± 0.21 |
| | fSNR | 2.78 ± 1.27 | 8.07 ± 5.40 |
| Inner | 3D VD | 0.40 ± 0.07 | 0.49 ± 0.07 |
| Outer | RA | 0.31 ± 0.07 | 0.19 ± 0.05 |

ICP: Intermediate capillary plexus, DCP: Deep capillary plexus, VD: Vessel density, fSNR: Flow signal-to-noise ratio, RA: Remaining artifacts.

As shown in Table 1, the described sacPR technique showed improvements (Table 1) over VD, fSNR on deeper plexus, as well as the 3D VD in inner retina volume and RA in outer retina, which indicated the sacPR preserved more flow signals and suppressed more background noise.

A better compensation technique should remove more projection artifacts and preserve more real flow signal. In original OCTA, projection artifacts are vascular patterns duplicated from anterior slabs. Large vessels' projection artifacts are significant and also more visually obvious due to the co-occurring shadow artifacts caused by the same vessels. These features make projection artifact removal more challenging under large vessels. To evaluate the performance, Pearson correlation coefficients r(x,y) were used to evaluate the similarity between anterior and posterior slabs (ICP vs. SVC and DCP vs. SVC&ICP) under the large vessels by:

$$r(x, y) = \frac{\sum_{i=1}^{n} (x_i - \overline{x})(y_i - \overline{y})}{\sqrt{\sum_{i=1}^{n} (x_i - \overline{x})^2} \sqrt{\sum_{i=1}^{n} (y_i - \overline{y})^2}} \tag{12}$$

where, x and y are two components to calculate correlation, i is the pixel index, n is the total number of pixels within the large vessel mask, r is between −1 and 1 that −1 and 1 means negatively and positively correlated, and 0 means no any correlation.

TABLE 2

Correlation between flow value underneath large vessels in original, reflectance-based PR and signal attenuation compensation compensated PR.

| | ICP | | DCP | |
|---|---|---|---|---|
| | $VD^+$ | $r^+$ | $VD^+$ | $r^+$ |
| Original | 0.85 ± 0.09 | 0.63 ± 0.05 | 0.77 ± 0.14 | 0.37 ± 0.13 |
| rbPR | 0.42 ± 0.11 | −0.07 ± 0.08 | 0.34 ± 0.10 | 0.02 ± 0.1 |
| sacPR | 0.78 ± 0.18 | 0.10 ± 0.06 | 0.70 ± 0.19 | 0.09 ± 0.07 |

ICP: Intermediate capillary plexus, DCP: Deep capillary plexus, $VD^+$: Vessel density under the large vessels, $r^+$: Pearson correlation coefficient between the current and upper slabs.

In original OCTA with projection artifacts, r is larger in both the ICP and DCP (Table 2). The higher r for ICP vs SVC also indicates projection artifacts are stronger in the ICP (FIG. 6 B1) than the DCP (FIG. 6 C1). Both the rbPR and sacPR techniques produced low r that is between −0.1 and 0.1, which indicates that projection artifacts have mostly been removed in deep slabs (Table 2). However, the VD is much higher with sacPR algorithm, which is due to the fact that sacPR preserved more flow signals.

Preservation on Challenging Scan Affected by Shadow Artifacts

Shadow artifacts are very common in real-world clinical data. OCTA flow signals are also decreased in shadowing area (FIG. 7C1) which makes it more difficult to remove projection artifacts in deeper slabs. Since the rbPR technique relies on vascular contrast in structural OCT, which can disappear in shadow affected regions, it can over-process both the projection artifacts and real flow signal in these regions (FIG. 7C2). The sacPR technique does not suffer from this limitation, and so more capillaries in both ICP (FIG. 7B3) and DCP (FIG. 7C3) are preserved. Moreover, sacPR showed better performance for removing projection artifacts (FIG. 7C3) that were not removed in rbPR (FIG. 7C2), as well as producing a clearer outer retina (FIG. 7D3). sacPR also generated more even CC and preserved more flow signals under large vessels (FIG. 7E3). These were over-processed by rbPR (FIG. 7E2).

Preservation on Pathological Scans

CNV is abnormal vessels in the normally avascular outer retina and results in exudation, hemorrhage, and fibrosis formation, each of which constitute a major threat of serious vision loss. OCTA as originally proposed was capable of detecting CNV, but doing so was difficult due to the presence of the strongly reflecting RPE nearby, which produces strong projection artifacts (FIG. 8D1). These artifacts are strong enough that it is simple to misinterpret some as CNV, and they can further cloak the real CNV vessels in spurious signal. Quantification of the lesion is virtually impossible under these conditions, but accurate quantification and monitoring of CNV dynamics is a clinical priority. The rbPR algorithm removed the strong projection artifacts, but remaining background can still interfere with CNV quantification. Moreover, the projection artifacts from the CNV itself are visible in the CC (FIG. 8E1) in both the original and rbPR OCTA result (FIG. 8E2). The sacPR OCTA technique removed the projection in inner retinal slabs (FIGS. 8A3-8C3) and suppressed more background noise in the outer retina (FIG. 8D3), as well as preserved more real CNV signals (FIG. 8D3). The projected CNV vascular patterns were also removed in CC (FIG. 8E3) and large vessel shadows in rbPR OCTA (FIG. 8E2) were also improved.

Platform Independence

The generalizability of the sacPR OCTA technique is important to apply to different OCTA systems. Since the sacPR OCTA technique may process the flow signals on each A-line, it is independent to OCTA devices and the image resolution. The platform independence was tested on the Zeiss angioplex OCTA and the latest Optovue Solix OCTA devices by adjusting three parameters: α and β in Equation (8) and $I_{th}$ in Equation (9).

Angioplex 3×3-mm macular scans has 245 A-lines in each B-scan and 245 B-scans in each volume, flow volume is generated utilizing an optical microangiography (OMAG) technique. The sacPR OCTA technique could remove the projections showing clear vasculature in deeper slabs (ICP&DCP, FIGS. 9B and 9C), and the tailed projection artifacts (FIG. 9D1) was suppressed in voxel (FIG. 9D2). The pathological symptoms of nonperfusion area and dilated vessel were also preserved.

The faster imaging speed on Optovue solix allows acquisition of the image in a wider area with dense A-lines. The Solix macular 9×9-mm has 600 A-lines in each B-scan and 600 B-scans in each volume. A wider imaging area was able to detect the neovascularization (NV) in the vitreous in the superior disc that was not caught in a 6×6-mm area. The dense A-lines showed distinct NV vessels (FIG. 10A1); however, the projection artifacts blocked capillary dropout in the SVC (FIG. 10B1). The sacPR OCTA technique was able to preserve the real NV flow and suppress the projection artifacts, revealing distinct twisted vessels in the SVC (FIG. 10B2), as well as the connection of NV to feeder vessels in cross-section (FIG. 10E2).

Example OCTA Image Processing System

Figure 11:
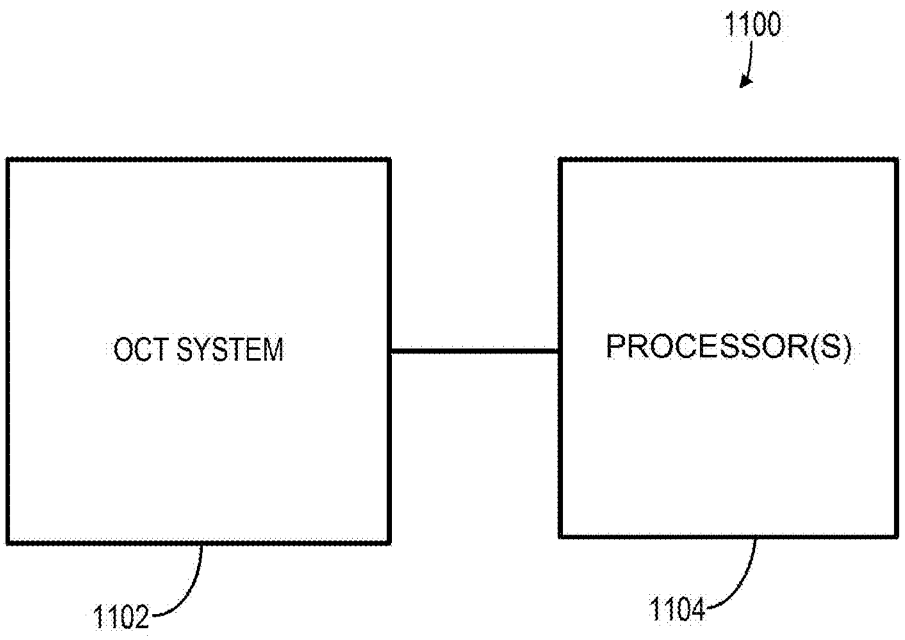
FIG. 11 schematically shows an example system for processing OCT and/or OCT angiography datasets to perform sacPR OCTA in accordance with the disclosure.

FIG. 11 schematically shows an example system 1100 for OCT image processing in accordance with various embodiments. System 1100 comprises an OCT system 1102 configured to acquire an OCT image comprising OCT interferograms and one or more processors or computing systems 1104 that are configured to implement the various processing routines described herein. OCT system 1100 can comprise an OCT system suitable for structural OCT and OCT angiography applications, e.g., a swept source OCT system or spectral domain OCT system.

In various embodiments, an OCT system can be adapted to allow an operator to perform various tasks. For example, an OCT system can be adapted to allow an operator to configure and/or launch various ones of the herein described methods. In some embodiments, an OCT system can be adapted to generate or cause to be generated, reports of various information including, for example, reports of the results of scans run on a sample.

In embodiments of OCT systems comprising a display device, data and/or other information can be displayed for an operator. In embodiments, a display device can be adapted to receive an input (e.g., by a touch screen, actuation of an icon, manipulation of an input device such as a joystick or knob, etc.) and the input can, in some cases, be communicated (actively and/or passively) to one or more processors. In various embodiments, data and/or information can be displayed, and an operator can input information in response thereto.

In some embodiments, the above described methods and processes can be tied to a computing system, including one or more computers. In particular, the methods and processes described herein can be implemented as a computer application, computer service, computer API, computer library, and/or other computer program product.

Figure 12:
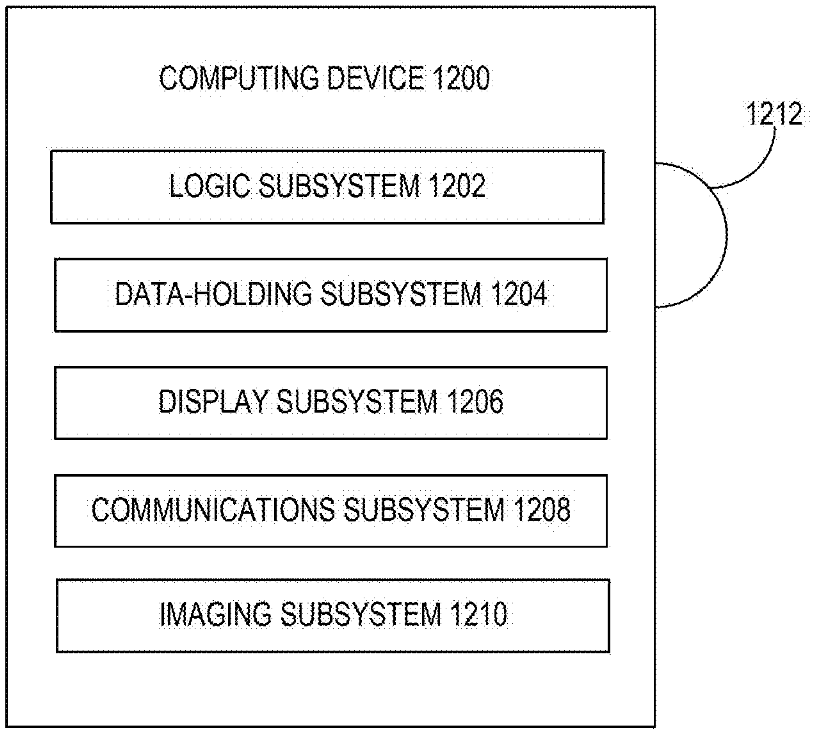
FIG. 12 schematically shows an example of a computing system in accordance with the disclosure.

FIG. 12 schematically shows a non-limiting computing device 1200 that can perform one or more of the above described methods and processes. For example, computing device 1200 can represent a processor included in system 1100 described above, and can be operatively coupled to, in communication with, or included in an OCT system or OCT image acquisition apparatus. Computing device 1200 is shown in simplified form. It is to be understood that virtually any computer architecture can be used without departing from the scope of this disclosure. In different embodiments, computing device 1200 can take the form of a microcomputer, an integrated computer circuit, printed circuit board (PCB), microchip, a mainframe computer, server computer, desktop computer, laptop computer, tablet computer, home entertainment computer, network computing device, mobile computing device, mobile communication device, gaming device, etc.

Computing device 1200 includes a logic subsystem 1202 and a data-holding subsystem 1204. Computing device 1200 can optionally include a display subsystem 1206, a communication subsystem 1208, an imaging subsystem 1210, and/or other components not shown in FIG. 12. Computing device 1200 can also optionally include user input devices such as manually actuated buttons, switches, keyboards, mice, game controllers, cameras, microphones, and/or touch screens, for example.

Logic subsystem 1202 can include one or more physical devices configured to execute one or more machine-readable instructions. For example, the logic subsystem can be configured to execute one or more instructions that are part of one or more applications, services, programs, routines, libraries, objects, components, data structures, or other logical constructs. Such instructions can be implemented to perform a task, implement a data type, transform the state of one or more devices, or otherwise arrive at a desired result.

The logic subsystem can include one or more processors that are configured to execute software instructions. For example, the one or more processors can comprise physical circuitry programmed to perform various acts described herein. Additionally or alternatively, the logic subsystem can include one or more hardware or firmware logic machines configured to execute hardware or firmware instructions. Processors of the logic subsystem can be single core or multicore, and the programs executed thereon can be configured for parallel or distributed processing. The logic subsystem can optionally include individual components that are distributed throughout two or more devices, which can be remotely located and/or configured for coordinated processing. One or more aspects of the logic subsystem can be virtualized and executed by remotely accessible networked computing devices configured in a cloud computing configuration.

Data-holding subsystem 1204 can include one or more physical, non-transitory, devices configured to hold data and/or instructions executable by the logic subsystem to implement the herein described methods and processes. When such methods and processes are implemented, the state of data-holding subsystem 1204 can be transformed (e.g., to hold different data).

Data-holding subsystem 1204 can include removable media and/or built-in devices. Data-holding subsystem 1204 can include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 1204 can include devices with one or more of the following characteristics: volatile, nonvolatile, dynamic, static, read/write, read-only, random access, sequential access, location addressable, file addressable, and content addressable. In some embodiments, logic subsystem 1202 and data-holding subsystem 1204 can be integrated into one or more common devices, such as an application specific integrated circuit or a system on a chip.

FIG. 12 also shows an aspect of the data-holding subsystem in the form of removable computer-readable storage media 1212, which can be used to store and/or transfer data and/or instructions executable to implement the herein described methods and processes. Removable computer-readable storage media 1212 can take the form of CDs, DVDs, HD-DVDs, Blu-Ray Discs, EEPROMs, flash memory cards, USB storage devices, and/or floppy disks, among others.

When included, display subsystem 1206 can be used to present a visual representation of data held by data-holding subsystem 1204. As the herein described methods and processes change the data held by the data-holding subsystem, and thus transform the state of the data-holding subsystem, the state of display subsystem 1206 can likewise be transformed to visually represent changes in the underlying data. Display subsystem 1206 can include one or more display devices utilizing virtually any type of technology. Such display devices can be combined with logic subsystem 1202 and/or data-holding subsystem 1204 in a shared enclosure, or such display devices can be peripheral display devices.

When included, communication subsystem 1208 can be configured to communicatively couple computing device 1200 with one or more other computing devices. Communication subsystem 1208 can include wired and/or wireless communication devices compatible with one or more different communication protocols. As non-limiting examples, the communication subsystem can be configured for communication via a wireless telephone network, a wireless local area network, a wired local area network, a wireless wide area network, a wired wide area network, etc. In some embodiments, the communication subsystem can allow computing device 1200 to send and/or receive messages to and/or from other devices via a network such as the Internet.

When included, imaging subsystem 1210 can be used acquire and/or process any suitable image data from various sensors or imaging devices in communication with computing device 1200. For example, imaging subsystem 1210 can be configured to acquire OCT image data, e.g., interferograms, as part of an OCT system, e.g., OCT system 1102 described above. Imaging subsystem 1210 can be combined with logic subsystem 1202 and/or data-holding subsystem 1204 in a shared enclosure, or such imaging subsystems can comprise periphery imaging devices. Data received from the imaging subsystem can be held by data-holding subsystem 1204 and/or removable computer-readable storage media 1212, for example.

Further Discussion of Various Embodiments

Various embodiments herein provide a novel PR OCTA algorithm—sacPR OCTA that removes flow projection artifacts and preserves in situ flow signals in OCTA, and demonstrate better results than the previously developed OCTA algorithm. In sacPR OCTA, signal attenuation factors were taken into account that both reflectance strength and optical length may be used to build up a flow signal attenuation model. Structural OCT shadows under the large vessels may be enhanced to fit the described model in the whole OCTA volume. Furthermore, 3D wavelet decompensation-based denoising method may be applied to suppress background noise and preserve vasculatures.

The previously developed rbPR OCTA algorithm was reliant on the vascular contrast in structural OCT, and the segmentation of inner/outer segment (IS/OS) that was used to divide the whole volume into two sub-volumes for vascular enhancement. However, vascular contrast can vanish in challenging scans affected by retinal pathologies, such as edema, and shadowing artifacts. Although the segmentation of ISOS is not required definitely accurate, manual review and correction are still necessary for challenging pathological areas, such as pigment epithelial detachment, subretinal fluid and subretinal hemorrhage. Compared to the rbPR OCTA algorithm, the described sacPR OCTA algorithm suppressed the projection artifacts in voxel-level and preserved more flow signals, and was also independent of image contrast and layer segmentation, which improved the robustness and would benefit the automatic vascular disease-related quantification, such as vessel density, non-perfusion area and CNV detection.

The technique described herein may be independent to platforms that can work well on different systems with different OCTA algorithms and imaging resolution.

The relationship between signal attenuation and reflectance and optical distance is complex. In the implementation described herein, the complex model may be simplified using a linear model, which is a limitation of the sacPR OCTA that a linear model may not fully describe the signal attenuation model on some challenging scans, such as low quality and pathological evaluation. In this case, the linear parameters can be adjusted individually to acquire the best PR OCTA data. A non-linear model may be able to further improve the PR OCTA.

It is to be understood that the configurations and/or approaches described herein are exemplary in nature, and that these specific embodiments or examples are not to be considered in a limiting sense, because numerous variations are possible. The specific routines or methods described herein can represent one or more of any number of processing strategies. As such, various acts illustrated can be performed in the sequence illustrated, in other sequences, in parallel, or in some cases omitted. Likewise, the order of the above-described processes can be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A method comprising:

receiving an optical coherence tomography angiography (OCTA) dataset;

determining, for respective voxels of the OCTA dataset, a proportion of in-situ flow signal based on a strength of attenuated projection artifacts in backscattered light;

adjusting respective values of the voxels based on the respective proportions to generate a signal attenuation-compensated projection-resolved OCTA (sacPR-OCTA) dataset; and generating a flow image based on the sacPR-OCTA dataset, wherein the strength of attenuated projection artifacts, $S_a$, is determined according to:

$$\begin{cases} A = g[R_{oct}(z),\ (z - z_0)] \\ S_a(z) = AS_i(z_0) \end{cases}$$

wherein A is a signal strength attenuation, $z_0$ and z correspond to depths in a A-line, $R_{oct}$ is a reflectance, $(z-z_0)$ is an optical path length, $S_i$ is an in-situ flow, and $g(\cdot)$ is a linear or non-linear model function.

2. The method of claim 1, wherein $g(\cdot)$ is the linear model function of:

$$S_{ea}(z) = \begin{cases} \left[\alpha R_{oct}(z) + \beta\left(1 - \frac{z - z_0}{D_{max}}\right)\right] S_i(z_0), & \text{if } (z - z_0) \le D_{max} \\ \alpha R_{oct}(z) S_i(z_0), & \text{if } (z - z_0) > D_{max} \end{cases}$$

wherein $S_{ea}$ is an estimated strength of projection artifacts, α is a coefficient of reflectance, and β is a coefficient of optical path length.

3. The method of claim 1, wherein the proportion of in-situ flow signal is determined according to:

$$p(z) = \mathrm{Nor}(S(z) - S_{ea}(z))$$

wherein S(z) is an observed value of the voxel at depth z, Nor is a normalization operator, and $S_{ea}(z)$ is an estimated projection artifacts strength at the depth z.

4. The method of claim 1, further comprising:

detecting voxels that correspond to vessels; and compensating the values of the detected voxels based on an intensity of respective surrounding voxels prior to determining the proportion of in-situ flow signal for the respective voxels.

5. The method of claim 4, wherein detecting the voxels that correspond to vessels includes:

classifying the voxels into a first category and a second category based on respective intensities of the voxels;

calculating a cumulative sum of voxels in the second category for each A-line in the OCTA dataset; and detecting the voxels that correspond to vessels as voxels associated with a cumulative sum that is greater than a threshold.

6. The method of claim 1, further comprising performing wavelet decomposition on the sacPR-OCTA dataset to suppress background noise.

7. The method of claim 6, wherein the wavelet decomposition is performed sequentially along a horizontal direction, a vertical direction, and a depth direction.

8. The method of claim 1, further comprising obtaining the OCTA dataset by measuring motion contrast using an amplitude or a phase of repeated structural B-scans acquired at a same scan location.

9. A system for optical coherence tomography angiography (OCTA) imaging, the system comprising:

an OCT system configured to acquire an OCTA dataset of a sample;

a logic subsystem; and a data holding subsystem comprising machine-readable instructions stored thereon that are executable by the logic subsystem to:

receive the OCTA dataset;

determine, for respective voxels of the OCTA dataset, a proportion of in-situ flow signal based on a strength of attenuated projection artifacts;

adjust respective values of the voxels based on the respective proportions to generate a signal attenuation-compensated projection-resolved OCTA (sacPR-OCTA) dataset, wherein the adjusting suppresses the attenuated projection artifacts; and generate a flow image based on the sacPR-OCTA dataset, wherein the strength of attenuated projection artifacts, $S_a$, is determined according to:

$$\begin{cases} A = g[R_{oct}(z),\ (z - z_0)] \\ S_a(z) = AS_i(z_0) \end{cases}$$

wherein A is a signal strength attenuation, $z_0$ and z correspond to depths in a A-line, $R_{oct}$ is a reflectance, $(z-z_0)$ is an optical path length, $S_i$ is an in-situ flow, and $g(\cdot)$ is a linear or non-linear model function.

10. The system of claim 9, wherein $g(\cdot)$ is the linear model function of:

$$S_{ea}(z) = \begin{cases} \left[\alpha R_{oct}(z) + \beta\left(1 - \frac{z - z_0}{D_{max}}\right)\right] S_i(z_0), & \text{if } (z - z_0) \le D_{max} \\ \alpha R_{oct}(z) S_i(z_0), & \text{if } (z - z_0) > D_{max} \end{cases}$$

wherein $S_{ea}$ is an estimated strength of projection artifacts, α is a coefficient of reflectance, and β is a coefficient of optical path length.

11. The system of claim 9, wherein the proportion of in-situ flow signal is determined according to:

$$p(z)=\mathrm{Nor}(S(z)-S_{ea}(z))$$

wherein S(z) is an observed value of the voxel at depth z, Nor is a normalization operator, and $S_{ea}(z)$ is an estimated projection artifacts strength at the depth z.

12. The system of claim 9, wherein the instructions are further executable by the logic subsystem to:

detect voxels that correspond to vessels; and compensate the values of the detected voxels based on an intensity of respective surrounding voxels prior to determining the proportion of in-situ flow signal for the respective voxels.

13. The system of claim 12, wherein to detect the voxels that correspond to vessels includes to:

classify the voxels into a first category and a second category based on respective intensities of the voxels;

calculate a cumulative sum of voxels in the second category for each A-line in the OCT data; and detect the voxels that correspond to vessels as voxels associated with a cumulative sum that is greater than a threshold.

14. The system of claim 9, wherein the instructions are further executable by the logic subsystem to perform wavelet decomposition on the sacPR-OCTA dataset to suppress background noise.

15. The system of claim 14, wherein the wavelet decomposition is performed sequentially along a horizontal direction, a vertical direction, and a depth direction.

16. The system of claim 9, wherein the OCTA dataset is acquired by measuring motion contrast using an amplitude or a phase of repeated structural B-scans acquired at a same scan location.

17. A method comprising:

receiving an optical coherence tomography angiography (OCTA) dataset;

determining, for respective voxels of the OCTA dataset, a proportion of in-situ flow signal based on a strength of attenuated projection artifacts in backscattered light;

adjusting respective values of the voxels based on the respective proportions to generate a signal attenuation-compensated projection-resolved OCTA (sacPR-OCTA) dataset;

generating a flow image based on the sacPR-OCTA dataset;

estimating a signal strength attenuation based on an optical path length; and determining the strength of attenuated projection artifacts based on the estimated signal strength attenuation.

18. A method comprising:

receiving an optical coherence tomography angiography (OCTA) dataset;

determining, for respective voxels of the OCTA dataset, a proportion of in-situ flow signal based on a strength of attenuated projection artifacts in backscattered light;

adjusting respective values of the voxels based on the respective proportions to generate a signal attenuation-compensated projection-resolved OCTA (sacPR-OCTA) dataset; and generating a flow image based on the sacPR-OCTA dataset, wherein the proportion of in-situ flow signal is determined according to:

$$p(z)=\mathrm{Nor}(S(z)-S_{ea}(z))$$

wherein S(z) is an observed value of the voxel at depth z, Nor is a normalization operator, and $S_{ea}(z)$ is an estimated projection artifacts strength at the depth z.

19. A method comprising:

receiving an optical coherence tomography angiography (OCTA) dataset;

determining, for respective voxels of the OCTA dataset, a proportion of in-situ flow signal based on a strength of attenuated projection artifacts in backscattered light;

adjusting respective values of the voxels based on the respective proportions to generate a signal attenuation-compensated projection-resolved OCTA (sacPR-OCTA) dataset;

generating a flow image based on the sacPR-OCTA dataset;

detecting voxels that correspond to vessels; and compensating the values of the detected voxels based on an intensity of respective surrounding voxels prior to determining the proportion of in-situ flow signal for the respective voxels, wherein detecting the voxels that correspond to vessels includes:

classifying the voxels into a first category and a second category based on respective intensities of the voxels;

calculating a cumulative sum of voxels in the second category for each A-line in the OCTA dataset; and detecting the voxels that correspond to vessels as voxels associated with a cumulative sum that is greater than a threshold.

20. A system for optical coherence tomography angiography (OCTA) imaging, the system comprising:

an OCT system configured to acquire an OCTA dataset of a sample;

a logic subsystem; and a data holding subsystem comprising machine-readable instructions stored thereon that are executable by the logic subsystem to:

receive the OCTA dataset;

determine, for respective voxels of the OCTA dataset, a proportion of in-situ flow signal based on a strength of attenuated projection artifacts;

adjust respective values of the voxels based on the respective proportions to generate a signal attenuation-compensated projection-resolved OCTA (sacPR-OCTA) dataset, wherein the adjusting suppresses the attenuated projection artifacts; and generate a flow image based on the sacPR-OCTA dataset, wherein the instructions are further executable by the logic subsystem to:

estimate a signal strength attenuation based on an optical path length; and determine the strength of attenuated projection artifacts based on the estimated signal strength attenuation.

21. A system for optical coherence tomography angiography (OCTA) imaging, the system comprising:

an OCT system configured to acquire an OCTA dataset of a sample;

a logic subsystem; and a data holding subsystem comprising machine-readable instructions stored thereon that are executable by the logic subsystem to:

receive the OCTA dataset;

determine, for respective voxels of the OCTA dataset, a proportion of in-situ flow signal based on a strength of attenuated projection artifacts;

adjust respective values of the voxels based on the respective proportions to generate a signal attenuation-compensated projection-resolved OCTA (sacPR-OCTA) dataset, wherein the adjusting suppresses the attenuated projection artifacts; and generate a flow image based on the sacPR-OCTA dataset, wherein the proportion of in-situ flow signal is determined according to:

$$p(z)=\mathrm{Nor}(S(z)-S_{ea}(z))$$

wherein S(z) is an observed value of the voxel at depth z, Nor is a normalization operator, and $S_{ea}(z)$ is an estimated projection artifacts strength at the depth z.

22. A system for optical coherence tomography angiography (OCTA) imaging, the system comprising:

an OCT system configured to acquire an OCTA dataset of a sample;

a logic subsystem; and a data holding subsystem comprising machine-readable instructions stored thereon that are executable by the logic subsystem to:

receive the OCTA dataset;

determine, for respective voxels of the OCTA dataset, a proportion of in-situ flow signal based on a strength of attenuated projection artifacts;

adjust respective values of the voxels based on the respective proportions to generate a signal attenuation-compensated projection-resolved OCTA (sacPR-OCTA) dataset, wherein the adjusting suppresses the attenuated projection artifacts; and generate a flow image based on the sacPR-OCTA dataset, wherein the instructions are further executable by the logic subsystem to:

detect voxels that correspond to vessels; and compensate the values of the detected voxels based on an intensity of respective surrounding voxels prior to determining the proportion of in-situ flow signal for the respective voxels, wherein to detect the voxels that correspond to vessels includes to:

classify the voxels into a first category and a second category based on respective intensities of the voxels;

calculate a cumulative sum of voxels in the second category for each A-line in the OCT data; and detect the voxels that correspond to vessels as voxels associated with a cumulative sum that is greater than a threshold.

* * * * *